United States Patent [19]

Reiffenrath et al.

[11] Patent Number: 5,389,291
[45] Date of Patent: Feb. 14, 1995

[54] 3,6-DISUBSTITUTED 2-HALOPYRIDINES

[75] Inventors: Volker Reiffenrath, Rossdorf; Thomas Geelhaar, Mainz, both of Germany

[73] Assignee: Merck Patent Gesellschaft mit beschrankter Haftung, Darmstadt, Germany

[21] Appl. No.: 828,949

[22] PCT Filed: Nov. 14, 1991

[86] PCT No.: PCT/EP91/02148

§ 371 Date: Feb. 11, 1992

§ 102(e) Date: Feb. 11, 1992

[87] PCT Pub. No.: WO92/09576

PCT Pub. Date: Jun. 11, 1992

[30] Foreign Application Priority Data

Nov. 27, 1990 [DE] Germany ............................ 4037630

[51] Int. Cl.⁶ ............................ C09K 19/34; G02F 1/13
[52] U.S. Cl. ............................ 252/299.61; 252/299.01; 359/103; 359/104
[58] Field of Search ................ 252/299.01, 299.61; 359/103, 104

[56] References Cited

U.S. PATENT DOCUMENTS

| | | | |
|---|---|---|---|
| 4,684,477 | 9/1986 | Sugimori et al. | 252/299.61 |
| 4,886,622 | 5/1988 | Miyazawa et al. | 252/299.61 |
| 4,913,838 | 9/1988 | Miyazawa et al. | 252/299.61 |
| 5,160,662 | 11/1992 | Satoh et al. | 252/299.61 |
| 5,204,477 | 4/1993 | Reiffenrath et al. | 546/303 |
| 5,205,962 | 4/1993 | Coates et al. | 252/299.61 |

FOREIGN PATENT DOCUMENTS

WO91/04248 4/1991 WIPO .

*Primary Examiner*—Shean Wu
*Attorney, Agent, or Firm*—Millen, White, Zelano & Branigan

[57] ABSTRACT

The invention relates to halopyridines of the formula I

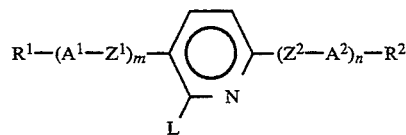

in which
L is Cl or F, and
$R^1$, $R^2$, $A^1$, $A^2$, $Z^1$, $Z^2$, m and n are as defined in patent claim 1, and the use thereof as components of liquid-crystalline, in particular ferroelectric, media.

13 Claims, No Drawings

3,6-DISUBSTITUTED 2-HALOPYRIDINES

FIELD OF THE INVENTION

The invention relates to 3,6-disubstituted 2-halopyridines of the formula I

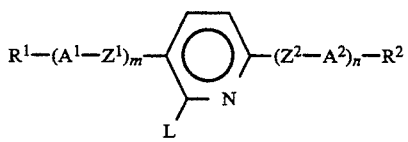

where
$R^1$ and $R^2$ are each, independently of one another, an alkyl or alkenyl radical having up to 15 carbon atoms which is unsubstituted or monosubstituted by CN, halogen or $CF_3$, it also being possible for one or more $CH_2$ groups in these radicals to be replaced, in each case independently of one another, by —S—, —O—, —CO—, —CO—O—, —O—CO— or —O—CO—O— in such a manner that S and/or O atoms are not linked directly to one another, and one of the radicals $R^1$ and $R^2$ is alternatively halogen, —$CF_3$, —$OCF_3$ or $OCHF_2$, $A^1$ and $A^2$ are each, independently of one another, a
(a) trans-1,4-cyclohexylene radical in which, in addition, one or more non-adjacent $CH_2$ groups may be replaced by —O— and/or —S—,
(b) 1,4-phenylene radical in which, in addition, one or two CH groups may be replaced by N,
(c) radical from the group comprising 1,3-cyclobutylene, 1,3-bicyclo[1.1.1]pentylene, 1,4-cylohexenylene [sic], 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by CN or halogen, $Z^1$ and $Z^2$ are each, independently of one another, —$CH_2$—$CH_2$—, —C≡C—, —$CH_2$O—, —$OCH_2$—, —CO—O—, —O—CO—, —CH=N—, —$CH_2$S—, —$SCH_2$—, a single bond or an alkylene group having 3 to 6 carbon atoms in which, in addition, one $CH_2$ group may be replaced by —O—, —CO—O—, —O—CO—, —CH-halogen- or —CHCN—, L is F or Cl,
m is 0, 1 or 2,
n is 0, 1 or 2, and
m+n is 1, 2 or 3, with the provisos that
a) in the case where L=F and $R^2$ is halogen, —$CF_3$, —$OCF_3$, $OCHF_2$ or alkoxy, n is 1 or 2, and/or
b) in the case where L=F and n=1 or 2,
$Z^2$ is —$CH_2CH_2$—, —C≡C—, —$CH_2$O—, —CO—O— or a single bond.

BACKGROUND OF THE INVENTION

Chiral tilted smectic liquid-crystalline phases having ferroelectric properties can be prepared by adding a suitable chiral dope to base mixtures having one or more tilted smectic phases (L. A. Beresnev et al., Mol. Cryst. Liq. Cryst. 89, 327 (1982); H. R. Brand et al., J. Physique 44 (lett.), L 771 (1983). Phases of this type can be used as dielectrics for fast-switching displays based on the principle of SSFLC technology described by Clark and Lagerwall (N. A. Clark and S. T. Lagerwall, Appl. Phys. Lett. 36, 899 (1980); U.S. Pat. No. 4,367,924) on the basis of the ferroelectric properties of the chirally [sic] tilted phase. The elongate molecules in this phase are arranged in layers, the molecules having a tilt angle to the layer normals. On moving from layer to layer, the tilt direction changes by a small angle with respect to an axis perpendicular to the layers, so that a helical structure is formed. In displays based on the principle of SSFLC technology, the smectic layers are arranged perpendicular to the plates of the cell. The helical arrangement of the tilt directions of the molecules is suppressed by a very small separation of the plates (about 1–2 μm). This forces the longitudinal axes of the molecules to line up in a plane parallel to the plates of the cell, which causes two preferential tilt alignments to be formed. Application of a suitable alternating electrical field allows switching back and forth between these two states in the liquid-crystalline phase having spontaneous polarization. This switching operation is significantly faster than in conventional twisted cells (TN-LCDs), which are based on nematic liquid crystals.

The currently available materials having chirally [sic] tilted smectic phases (such as, for example, Sc* [sic ], but also $S_H^*$, $S_I^*$, $S_J^*$, $S_K^*$, $S_G^*$ and $S_F^*$) has the great disadvantage for many applications of low chemical, thermal and photostability. A further disadvantageous property of displays based on currently available chirally [sic] tilted smectic mixtures is that the spontaneous polarization has values which are too low, so that the response time behavior of the displays is adversely affected and/or the pitch and/or the tilt and/or the viscosity of the phases does not meet the requirements of display technology. In addition, the temperature range of the ferroelectric phases is usually too small and is predominantly at excessively high temperatures.

SUMMARY OF THE INVENTION

It has now been found that the use of compounds of the formula I as components of chirally [sic] tilted smectic mixtures can significantly reduce said disadvantages. The compounds of the formula I are thus eminently suitable as components of chirally [sic] tilted smectic liquid-crystalline phases. They can be used, in particular, to prepare chirally [sic] tilted smectic liquid-crystalline phases which are particularly stable chemically and have favorable ferroelectric phase ranges, favorable distances [sic] for the viscosity, in particular having broad Sc* [sic] phase ranges, excellent supercoolability down to temperatures below 0° C. without crystallization occurring, and values for the spontaneous polarization which are moderate to high for phases of this type. P is the spontaneous polarization in $nC/cm^2$. However, the compounds of the formula I are also suitable for liquid-crystalline $S_A$ phases for the electroclinic effect.

The compounds of the formula I have negative anisotropy of the dielectric constants (Δε= −0.2 to −5.0) at the same time as a high dielectric constant perpendicular to the longitudinal axis of the molecule ($ε_⊥$) [lacuna] therefore have a broad range of applications. Depending on the choice of substituents, these compounds can be used as base materials from which liquid-crystalline smectic phases are predominantly composed; however, compounds of the formula I can also be added to liquid-crystalline base materials from other classes of compound in order, for example, to vary the dielectric and/or optical anisotropy and/or the viscosity and/or the spontaneous polarization and/or the phase range and/or the tilt angle and/or the pitch of a dielectric of this type.

Similar compounds are disclosed, for example, in the international Patent Application WO 88/07992. These contain a 2-chloro-3-cyanopyridin-6-yl group, are employed as intermediates in the preparation of compounds containing a 4-cyanopyridin-6-yl group and are not suitable as components of chirally [sic] tilted, smectic liquid-crystalline media.

The compounds excluded by provisos a) and b) are the subject-matter of the international Application PCT/EP 90/01536, which is not a prior publication. These are not suitable for ferroelectric displays.

The optically active compounds of the formula I are covered by the general formula, for example, of EP-0 283 326-A. However, a person skilled in the art is able to deduce from this application neither the advantageous properties of the compounds according to the invention nor methods for their preparation.

A person skilled in the art was thus able to deduce from the prior art in a simple manner neither possible syntheses for the compounds claimed nor that the compounds according to the invention have predominantly broad and favorably located $S_c$ phases and are distinguished by favorable values for the rotational viscosity.

The invention thus relates to the 2-halopyridines of the formula I, in particular in which n is 1 or 2, and at least one of the radicals $A^1$ and $A^2$ is optionally fluorine-substituted 1,4-phenylene, 1,4-cyclohexylene, pyrimidine-2,5-diyl or pyridine-2,5-diyl.

The compounds of the formula I include the bicyclic compounds of the formula [sic] I1–I4

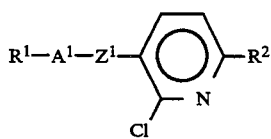

I1

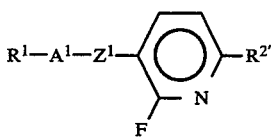

I2

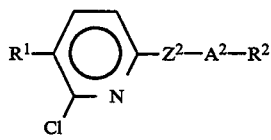

I3

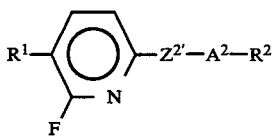

I4 in which $R^1$, $R^{12}$, $A^1$, $A^1$, $Z^1$ and $Z^2$, are as defined above, and $R^2$, is unsubstituted alkyl, oxaalkyl or dioxaalkyl, or alkyl or alkoxy which is monosubstituted by CN, halogen or $CF_3$, and $Z^2$ is $-CH_2CH_2-$, $-C-C-$, $-CH_2O-$, $-CO-O-$ or a single bond, tricyclic compounds of the formulae I5 to I10

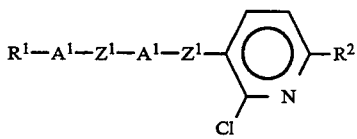

I5

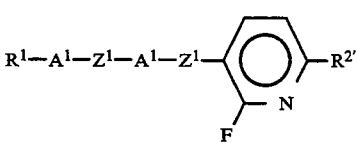

I6

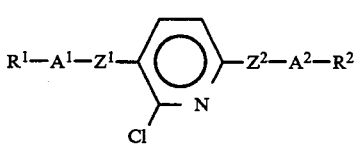

I7

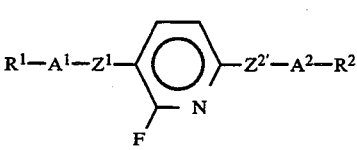

I8

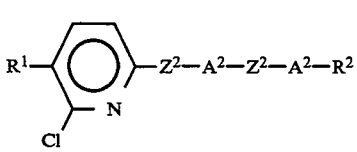

I9

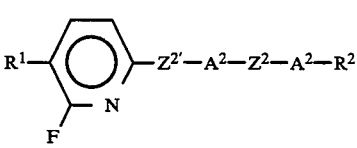

I10 and tetracyclic compounds of the formula I11 to I12.

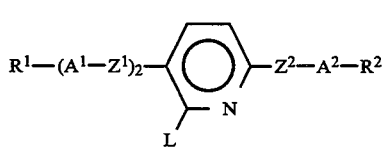

I11

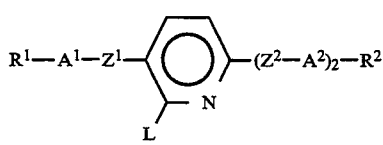

I12

The invention furthermore relates to a process for the preparation of the compounds of the formula IZ

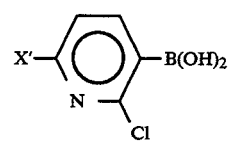

IZ in which

X' is H, Cl, alkyl, alkoxy, oxaalkyl or dioxaalkyl having 1 to 12 carbon atoms,
characterized in that 2-chloro- or 2,6-dichloropyridine is treated in an inert solvent with a strong base, preferably lithium diisopropylamide, subsequently reacted with trimethyl borate and acidified.

The invention furthermore relates to the compounds of the formula IZ.

The compounds are highly suitable for the preparation of the compounds of the formula I (cf. Schemes 1 and 3).

The invention also relates to the use of the compounds of the formula I in which L is Cl for the preparation of the compounds of the formula II, $$R^1-(A^1-Z^1)_m-\underset{N}{\underset{|}{\bigcirc}}-(A^2-Z^2)_n-R^2 \quad \text{II}$$

in which $R^1$, $R^2$, $A^1$, $A^2$, $Z^1$, $Z^1$, m and n are as defined for formula I.

The compounds of the formula II are known per se (for example WO 87/04158), but the processes described hitherto only result in unsatisfactory yields.

To prepare the compounds of the formula II, the compounds of the formula I in which L is Cl are treated in an inert solvent with complex hydrides or hydrogenated in the presence of a transition-metal catalyst.

The invention relates, in particular, to optically active halopyridines of the formula I in which one of the radicals $R^1$ and $R^2$ is a chiral group of the formula III $$R^4-\underset{\underset{Y}{|}}{\overset{\overset{R^o}{|}}{C}}-Z \quad \text{III}$$

where
$R^4$ is a group of the formula $(CH_2)_s-Q^3-C_oH_{2o+1}$, in which
  $Q^3$ is —O—, —O—CO— or a single bond,
  s is 0, 1 or 2, and
  o is 1 to 7,
Y is CN, halogen or $CH_3$,
Z is a single bond or —$(CH_2)_p$— in which one $CH_2$ group may be replaced by —O—, —O—CO— or —CO—O—, and p is 1, 2, 3, 4, 5 or 6, and
$R^o$ is H or $CH_3$,
with the proviso that only one of the groups $R^o$, $R^4$ and Y is $CH_3$. The invention furthermore relates to liquid-crystalline phases which contain at least one compound of the formula I. The invention moreover relates to ferroelectric liquid-crystalline phases containing at least one compound which [lacuna] a group of the formula [lacuna]

$$-\underset{\underset{L}{|}}{\underset{N}{\bigcirc}}-$$

of the formula I and liquid-crystal display elements, in particular ferroelectric electrooptical display elements, which contain phases of this type.

The phases according to the invention preferably contain at least two, in particular at least three, compounds of the formula I. Particular preference is given to chiral tilted smectic liquid-crystalline phases according to the invention whose achiral base mixture, in addition to compounds of the formula I, contains at least one other component having negative or small positive dielectric anisotropy. This further component or these further components of the achiral base mixture can make up from 1 to 50%, preferably from 10 to 25%, of the base mixture. Suitable further components having small positive or negative dielectric anisotropy are compounds of the formula IV, which include the compounds of the subformulae IVa to IVi:

$$R^4-\bigcirc-COX-\bigcirc-R^5 \quad \text{IVa}$$

$$R^4-\bigcirc-COX-\bigcirc-R^5 \quad \text{IVb}$$

$$R^4-\bigcirc-COX-\bigcirc-R^5 \quad \text{IVc}$$

$$R^4-\bigcirc-\bigcirc-COX-\bigcirc-R^5 \quad \text{IVd}$$

$$R^4-\bigcirc-\bigcirc-COX-\bigcirc-R^5 \quad \text{IVe}$$

$$R^4-\bigcirc-COX-\bigcirc-\bigcirc-R^5 \quad \text{IVf}$$

$$R^4-\bigcirc-COX-\bigcirc-\bigcirc-R^5 \quad \text{IVg}$$

$$R^4-\bigcirc-\bigcirc-COO-\bigcirc-R^5 \quad \text{IVh}$$

$$R^4-\bigcirc-\bigcirc-COO-\bigcirc-R^5 \quad \text{IVi}$$

$R^4$ and $R^5$ are each preferably straight-chain alkyl, alkoxy, alkanoyloxy or alkoxycarbonyl, in each case having 3 to 12 carbon atoms. X is preferably O. In the compounds of the formulae IVa, IVb, IVd, IVe, IVf and IVg, it is also possible for one 1,4-phenylene group to be laterally substituted by halogen or CN, particularly preferably by fluorine.

Particular preference is given to the compounds of the subformulae IVa, IVb, IVd and IVf in which $R^4$ and $R^5$ are each straight-chain alkyl or alkoxy, in each case having 5 to 10 carbon atoms. Particularly preferred individual compounds are indicated in Table I below:

TABLE I

| Formula | $R^4$ | $R^5$ | X |
|---|---|---|---|
| IVa | n-decyloxy | n-heptyloxy | O |
| IVa | n-hexyloxy | n-decyloxy | O |
| IVa | n-octyloxy | n-heptyl | O |
| IVa | n-octyloxy | n-pentyl | O |
| IVa | n-decyloxy | n-heptyl | O |
| IVa | n-decyloxy | n-pentyl | O |
| IVf | n-pentyl | n-pentyl | O |
| IVf | n-pentyl | n-hexyl | O |

The compounds of the subformulae IVc, IVh and IVi are suitable as additives for reducing the melting point and are normally added to the base mixtures in an amount of not more than 5%, preferably from 1 to 3%. $R^4$ and $R^5$ in the compounds of the subformulae IVc, IVh and IVi are preferably straight-chain alkyl having 2 to 7, preferably 3 to 5, carbon atoms. A further class of compounds which is suitable for reducing the melting point in the phases according to the invention is that of the formula

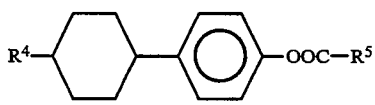

in which $R^4$ and $R^5$ have the preferred meaning indicated for IVc, IVh and IVi.

Suitable further components having negative dielectric anisotropy are furthermore compounds containing the structural element A, B or C.

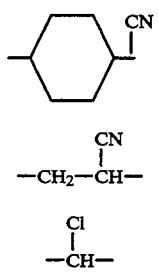

Preferred compounds of this type conform to the formulae Va, Vb and Vc:

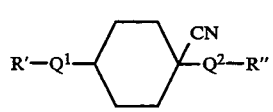

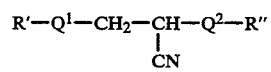

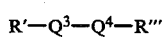

R' and R" are each preferably straight-chain alkyl or alkoxy groups, in each case having 2 to 10 carbon atoms. $Q^1$ and $Q^2$ are each 1,4-phenylene, trans-1,4-cyclohexylene, 4,4'-biphenylyl, 4-(trans-4-cyclohexyl)phenyl, trans,trans-4,4'-bicyclohexyl or one of the groups $Q^1$ and $Q^2$ is alternatively a single bond.

$Q^3$ and $Q^4$ are each 1,4-phenylene, 4,4'-biphenylyl or trans-1,4-cyclohexylene. One of the groups $Q^3$ and $Q^4$ can alternatively be 1,4-phenylene in which at least one CH group has been replaced by N. R''' is an optically active radical containing an asymmetric carbon atom of the structure

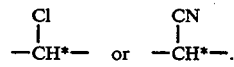

Particularly preferred compounds of the formula Vc are those of the formula Vc'

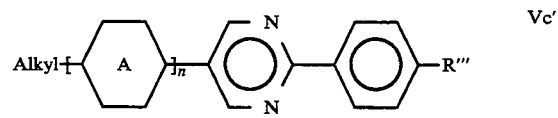

in which A is 1,4-phenylene or trans-1,4-cyclohexylene, and n is 0 or 1.

Particular preference is given to ferroelectric liquid-crystalline phases which contain at least one achiral halopyridine of the formula I1, at least one achiral phenylpyrimidine of the formula Vc' in which R''' is an alkyl or alkoxy radical having up to 18 carbon atoms, as the base material having a broad $S_c$ phase and at least one chiral halopyridine of the formula I as optically active dope. Preference is furthermore given to ferroelectric liquid-crystalline phases which, in addition to said compounds of the formula I1, Vc' and I, contain at least one phenylpyridine of the formula Vd and/or a 2-fluoro- (L=H) or 2,3-difluorophenylpyrimidine of the formula Ve (L=F) and/or a phenylpyrimidine of the formula Vf

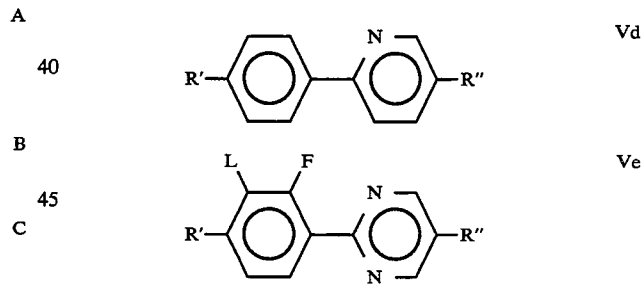

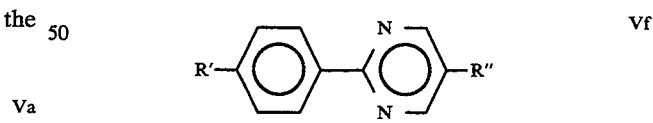

The achiral halopyridines of the formula IA

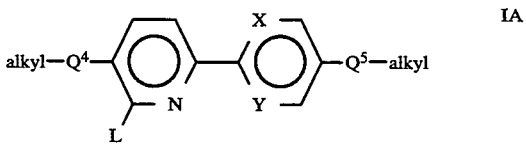

in which alkyl is in each case, independently of one another, alkyl having 1 to 18 carbon atoms, X and Y are each, independently of one another, CH or N, $Q^4$ is

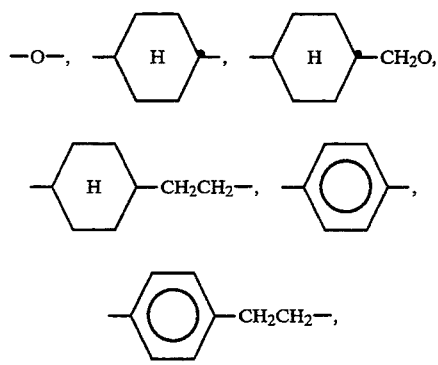
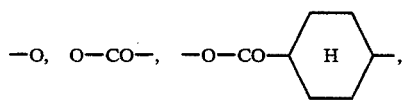
or a single bond, and
Q⁵ is
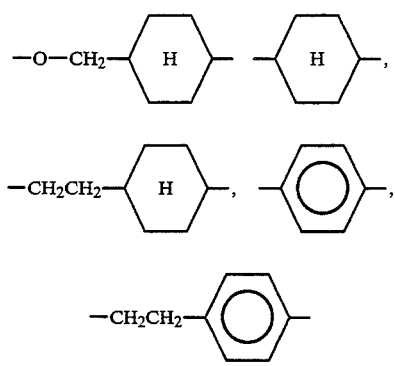
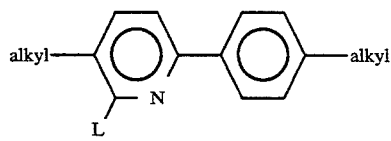
or a single bond,
-continued
or a single bond, are particularly suitable as constituents of smectic base materials.
The compounds of the formula IA include the achiral preferred [sic] bicyclic and tricyclic materials of the formulae IA1 to IA18 listed below
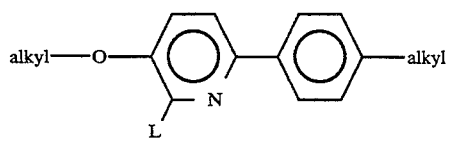
IA1
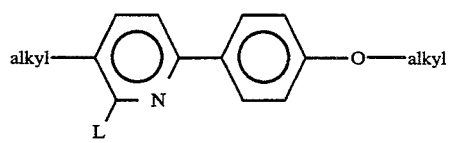
IA2
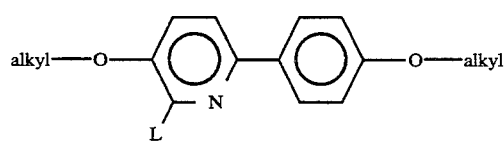
IA3
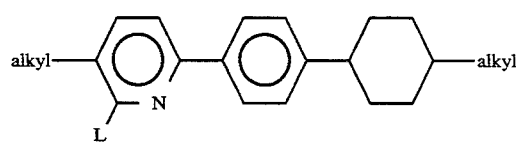
IA4
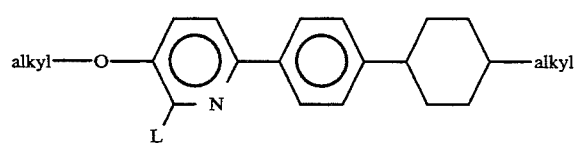
IA5
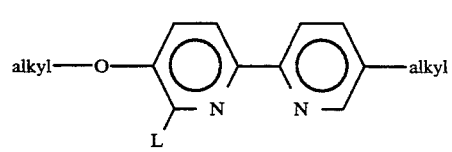
IA6
IA7

-continued
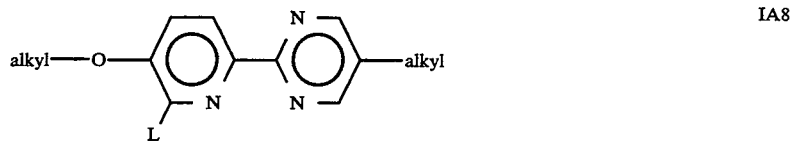 IA8
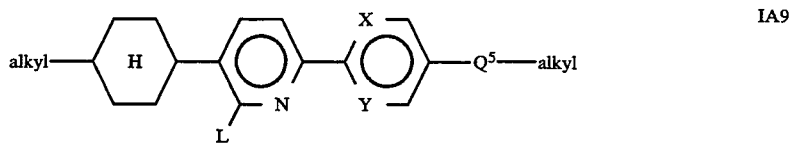 IA9
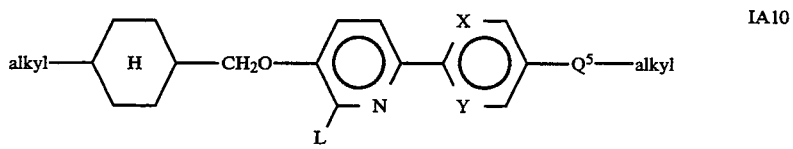 IA10
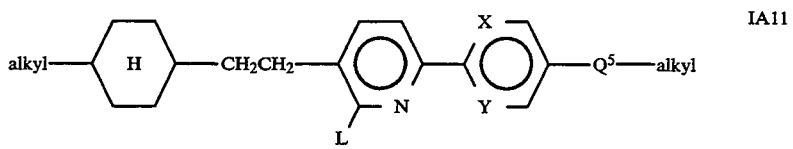 IA11
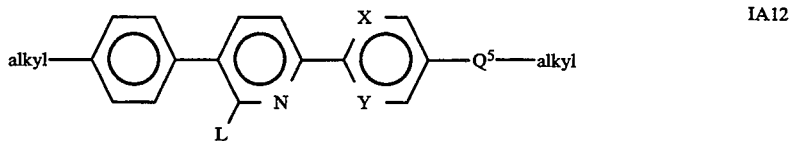 IA12
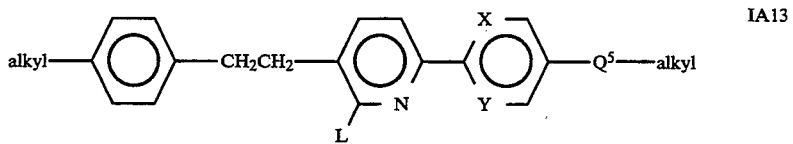 IA13
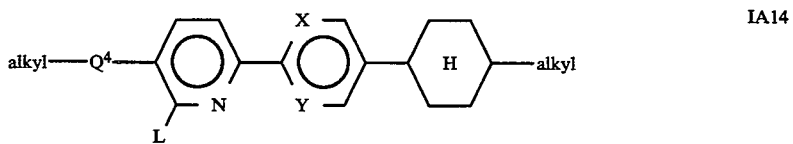 IA14
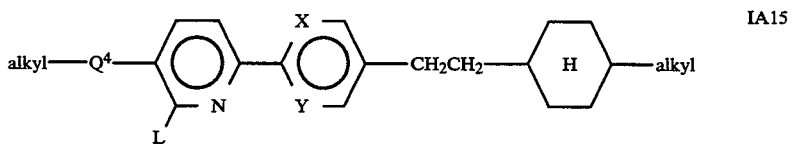 IA15
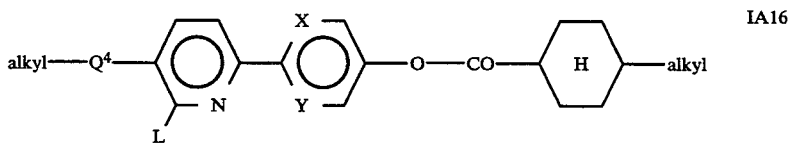 IA16
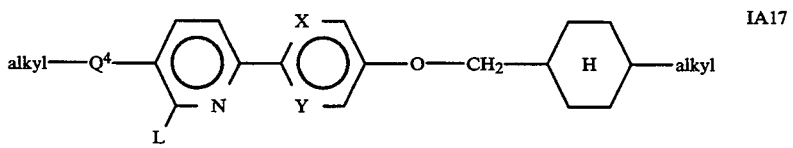 IA17

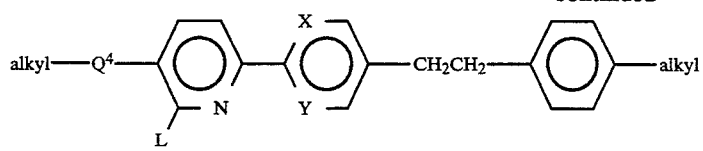

where, in the compounds IA9 to IA18, $Q^4$ is —O— or a single bond and $Q^5$ is —O—, —O—CO— or a single bond, and X and Y are each, independently of one another, N or CH, preferably CH.

Furthermore preferred compounds of the formula I are those of the formulae [sic] IB

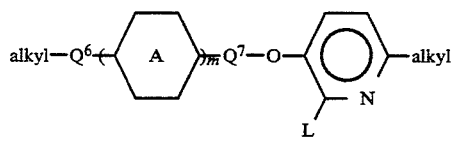

in which
alkyl is in each case, independently of one another, alkyl having 1 to 18 carbon atoms,
$Q^6$ is —O—, —CO—O—, —O—CO— or a single bond,
$Q^7$ is —CO— or —CH$_2$—,

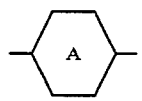

is in each case, independently of one another,

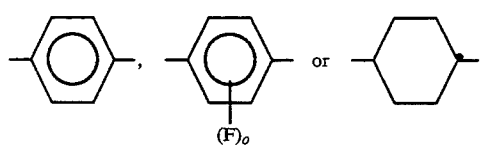

where o is 0, 1 or 2, and
m is 1 or 2.

These compounds of the formula IB are particularly suitable as constituents of nematic mixtures.

The compounds of the formula IB include the preferred [sic] bicyclic and tricyclic materials of the formula [sic] IB1 to IB8 listed below:

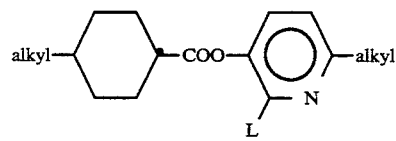

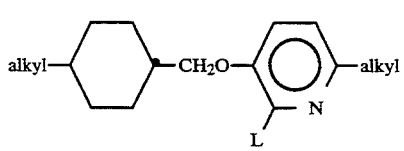

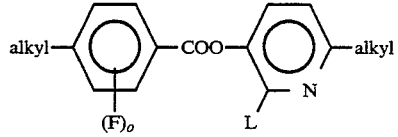

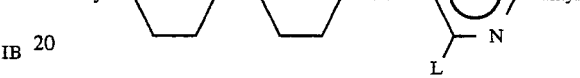

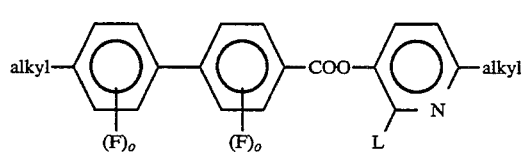

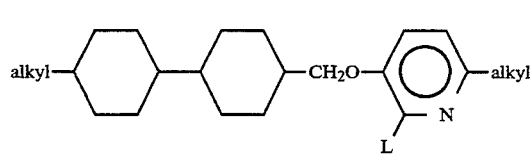

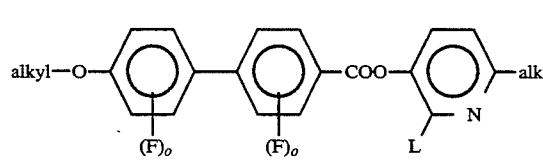

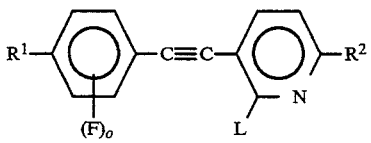

Furthermore preferred compounds of the formula I are those in which the radical $Z^1$ or $Z^2$ linked to the 6-halopyridine-2,5-diyl is a —C≡C— group and $A^1$ and/or $A^2$ is 1,4-phenylene, which is optionally substituted by 1 or 2 fluorine atoms, or 1,4-cyclohexylene. These compounds include the preferred compounds of the formulae IT1 to IT6,

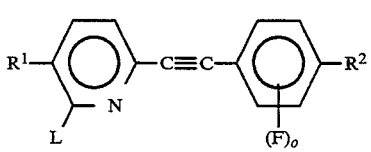

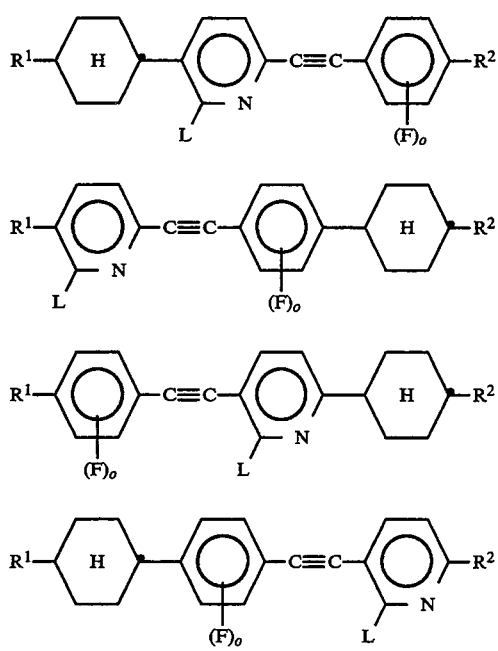

in which
o is 0, 1 or 2.

In the preferred compounds of the formula [sic] IT1 to IT6, L is preferably F and o is 0; particular preference is given to the compounds of the formula [sic] IT2 and IT4 in which L is F and $R^1$ is alkoxy having 1 to carbon atoms.

The compound [sic] of the formula [sic] IT1 to IT6 are particularly suitable as components of nematic phases for ECB or STN displays.

In the formulae above and below, $R^1$ and $R^2$ preferably have 1–13 carbon atoms, in particular 3–12 carbon atoms. Compounds of the formula I in which $R^1$ and $R^2$ have 1–7 carbon atoms, preferably 1–5 carbon atoms, are particularly suitable for liquid-crystalline phases for display elements based on the ECB effect. By contrast, compounds of the formula I in which $R^1$ and $R^2$ have 6–15 carbon atoms, preferably 6–12 carbon atoms, are suitable for liquid-crystalline phases having ferroelectric properties. It is also possible for one or two $CH_2$ groups in $R^1$ and $R^2$ to have been replaced. It is preferred that only one $CH_2$ group has been replaced by —O—, —S—, —CO—O— or —O—CO—, in particular by —O—.

Preference is furthermore given to compounds in which 2, 3 or [lacuna] non-adjacent $CH_2$ groups have been replaced by —O—.

In the formulae above and below, $R^1$ and $R^2$ are preferably alkyl, alkoxy or another oxaalkyl group.

If $R_1$ [sic] and $R_2$ [sic] are alkyl radicals in which one ("alkoxy" or "oxaalkyl") or two ("alkoxyalkoxy" or "dioxaalkyl") non-adjacent $CH_2$ groups may also have been replaced by O atoms, they may be straight-chain or branched. They are preferably straight-chain, have 2, 3, 4, 5, 6 or 7 carbon atoms and accordingly are preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, tridecoxy or tetradecoxy.

Oxalkyl is preferably straight-chain 2-oxypropyl [sic] (=methoxymethyl), 2- (=ethoxymethyl) or 3-oxabutyl (=2 methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

The compounds of the formula I which contain one or two dioxa- or trioxaalkyl group [sic] are particularly suitable as complexing podands for reducing the concentration of free ions in liquid-crystalline mixtures, in particular for ferroelectric displays. In particular, these compounds can be used to suppress so-called "ghost images" (cf., for example, J. Dijon et al., SID conference, San Diego 1988, pages 2–249).

If $R^1$ and $R^2$ are an alkyl radical in which one $CH_2$ group has been replaced by —S—, this may be straight-chain and [sic] branched. This thiaalkyl radical is preferably straight-chain and is 2-thiapropyl, 2- or 3-thiabutyl, 2-, 3- or 4-thiapentyl, 2-, 3-, 4- or 5-thiahexyl, 2-, 3-, 4-, 5- or 6-thiaheptyl, 2-, 3-, 4-, 5-, 6- or 7-thiaoctyl, 2-, 3-, 4-, 5-, 6-, 7- or 8-thianonyl or 2-, 3-, 4-, 5-, 6-, 7-, 8- or 9-thiadecyl.

Particularly preferred alkyl radicals $R^1$ or $R^2$ are those in which the $CH_2$ group adjacent to the $A^1$ $A^2$ and/or $A^3$ group has been replaced by —S— and is thus preferably methylthio, ethylthio, propylthio, butylthio, pentylthio, hexylthio, heptylthio, octylthio, nonylthio or decylthio.

If $R^1$ and $R^2$ are an alkenyl radical, this may be straight-chain or branched. It is preferably straight-chain and has 2 to 10 carbon atoms. It is accordingly particularly vinyl, prop-1- or prop-2-enyl, but-1-, 2- or but-3-enyl, pent-1-, 2-, 3- or pent-4-entyl [sic], hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7-or non-8-enyl, or dec-1-, 2-, 3-, 4-, 5-, 6-, 7-, 8-or dec-9-enyl.

If $R^1$ and $R^2$ are an alkyl radical in which one $CH_2$ group has been replaced by —O—CO or —CO—O—, this may be straight-chain or branched. It is preferably straight-chain and has 2 to 6 carbon atoms. It is accordingly particularly acetyloxy, propionyloxy, butyryloxy, pentanoyloxy, hexanoyloxy, acetyloxymethyl, propionyloxymethyl, butyryloxymethyl, pentaoyloxymethyl [sic], 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

Compounds of the formula I containing branched wing groups $R^1$ and/or $R^2$ may occasionally be of importance due to better solubility in the conventional liquid-crystalline base materials, but in particular as chiral dopes if they are optically active. Smectic compounds of this type are suitable as components of ferroelectric materials.

Branched groups of this type generally contain not more than one chain branch. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

Particular preference is given to the compounds of the formula I in which L=F, m=0 and $R^1$ and $R^2$ are each, independently of one another, alkyl having up to 15 carbon atoms in which, in addition, one or more $CH_2$ groups may have been replaced by 0 [sic] atoms. $R^1$ is preferably alkoxy having up to 12 carbon atoms.

The chiral halopyridines of the formula I in which one of the radicals $R^1$ and $R^2$ is a group of the formula III are highly suitable as dopes for inducing ferroelectricity in a smectic base material. They are distinguished, in particular, by high spontaneous polarization.

Furthermore, they do not destabilize the smectic phase of these base materials. The radical of the formula III is referred to below as R*.

The chiral compounds of the formula I accordingly include the bicyclic compounds of the subformulae Ic1 to Ic4

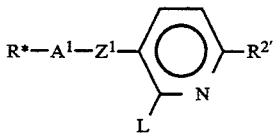
Ic1

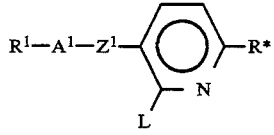
Ic2

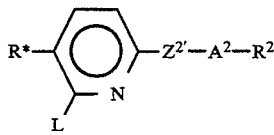
Ic3

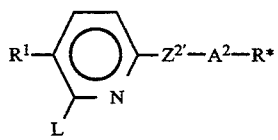
Ic4 and the tricyclic compounds of the formulae Ic5 to Ic10:

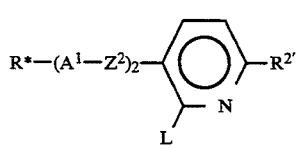
Ic5

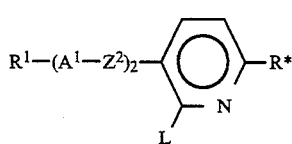
Ic6

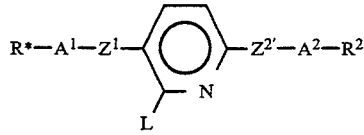
Ic7

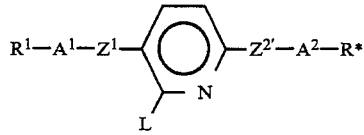
Ic8

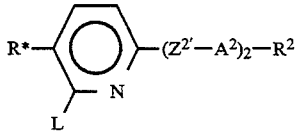
Ic9

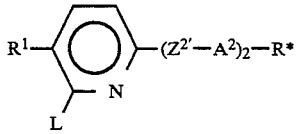
Ic10 in which $R^1$, $R^2$, L $Z^2$ and $Z^{2'}$, are as defined above, and $R^{2'}$, in the case where L=Cl, has the same meaning as $R^2$, but in the case where L=F, where halogen, —$CF_3$, —$OCF_3$, —$OCHF_2$ and alkoxy are excluded. In the case where L=Cl, $Z^{2'}$ has the same meaning as $Z^2$ and in the case where L=F, $Z^{2'}$ is —$CH_2CH_2$—, —C—C—, —$CH_2O$—, —CO—O— or a single bond.

Particularly preferred compounds are those of the subformulae Ic1 to Ic4 in which $R^1$ and $R^2$ are each alkyl or alkoxy having 1 to 12 carbon atoms or $R^{2'}$ is alkyl, oxaalkyl or dioxaalkyl having 1 to 12 carbon atoms, and $A^1$ or $A^2$ is 1,4-phenylene in which, in addition, 1 or 2 CH groups may have been replaced by N.

Of these, particular preference is given to the chiral compounds of the formula I in which R* is a group of the formula IIIa

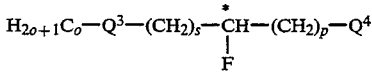
IIIa in which o and $Q^3$ are as defined above, $Q^4$ is —O—, —CO—O— or a single bond, r is 1 or 2, and p is 0 or 1.

The chiral radicals of the formula IIIa accordingly include the chiral monofluoroalkyl, monofluoroaoxaalkyl [sic] and alkanoyloxymonofluoroalkyl group $R_f^*$ of the formulae IIIa1 to IIIa6:

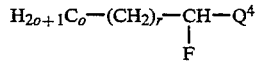
IIIa1

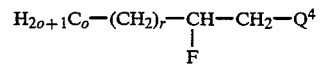
IIIa2

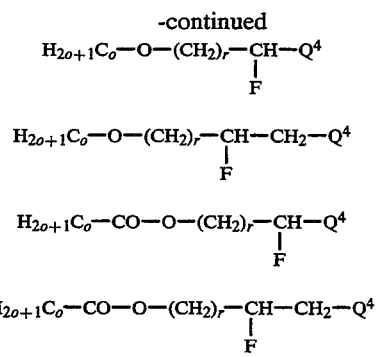

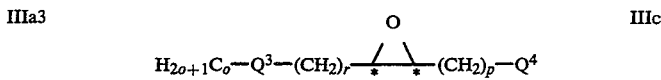

in which $Q^3$, $Q^4$, r and p are as defined above.

The compounds of the formula I are prepared by methods which are known per se, as described in the literature (for example in the standard works such as Houben-Weyl, Methoden der Organischen Chemie, Georg-Thieme-Verlag, Stuttgart).

Of the chiral monofluoro groups $R_f^*$ of the formulae IIIa1 to IIIa6, particular preference is given to those of the formulae IIIa1, IIIa3 and IIIa5, in particular those in which r is 2.

If desired, the starting materials can also be formed in situ by not isolating them from the reaction mixture, but instead immediately further converting them into the compounds of the formula I.

The compounds according to the invention can easily be prepared in accordance with the reaction schemes (1–9 [sic]) below.

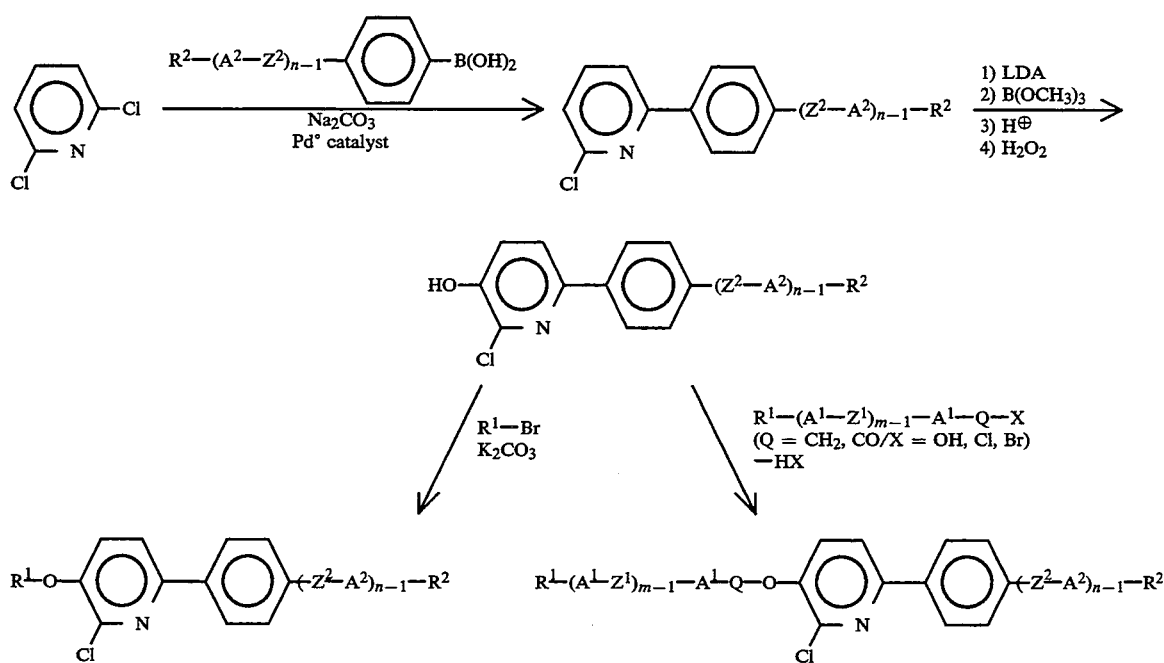

Preference is furthermore given to the chiral compounds of the formula I in which R* is a group of the formula IIIb

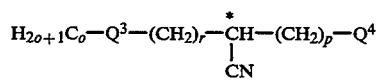

in which o, $Q^3$ and $Q^4$ are as defined above, r is 1 or 2, and p is 0 or 1.

Preference is furthermore given to the compounds of the formula I in which R* is a group of the formula IIIc

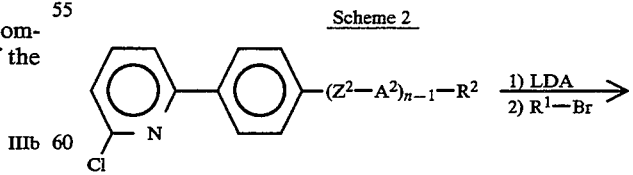

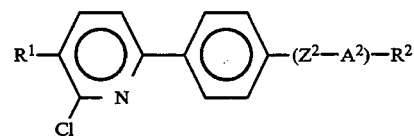

5,389,291
Scheme 2
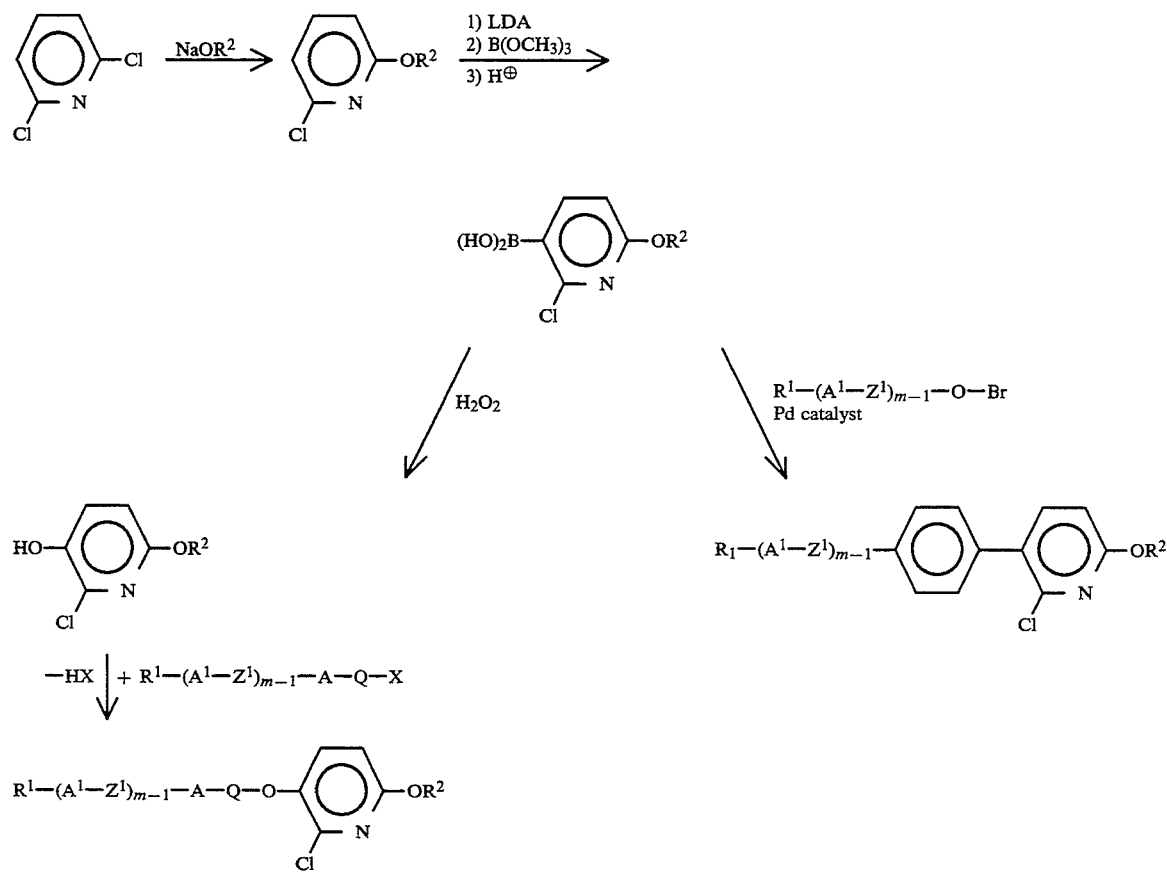
Scheme 4
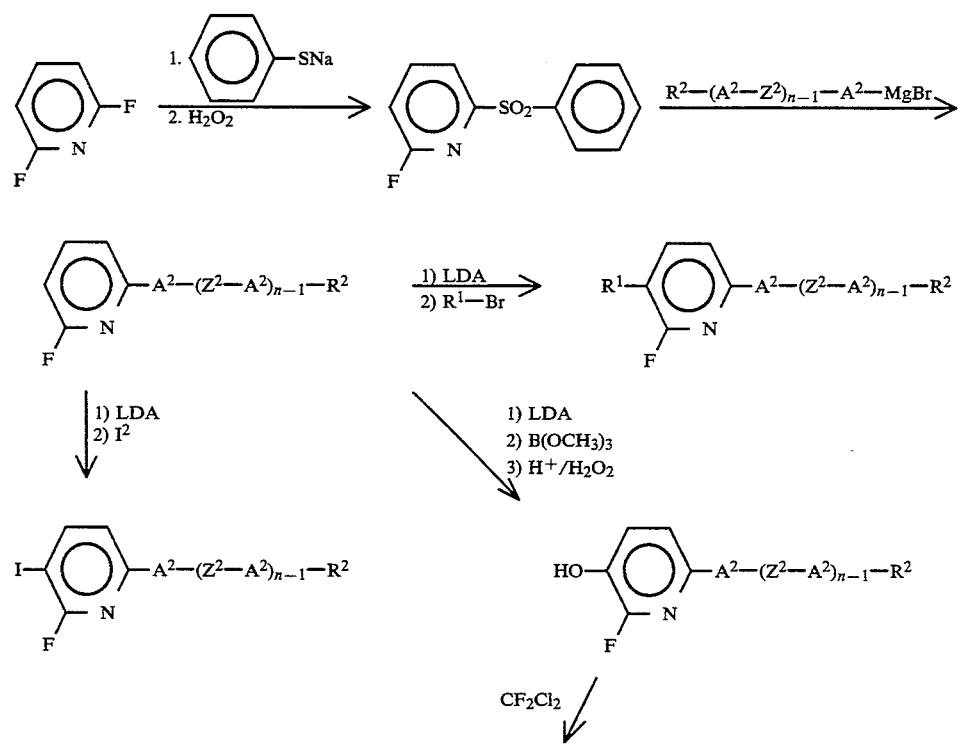

-continued
Scheme 4
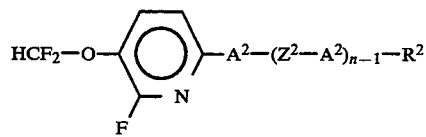
Scheme 5
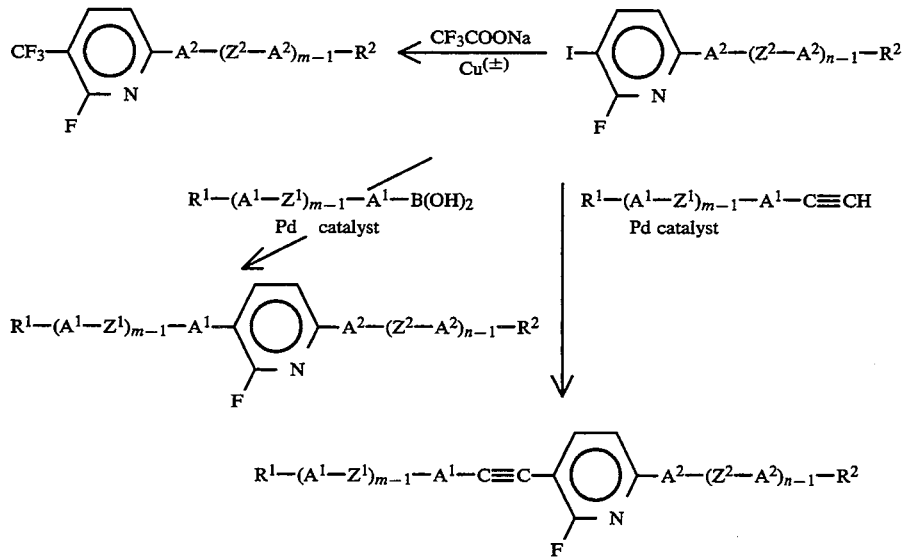
Scheme 6
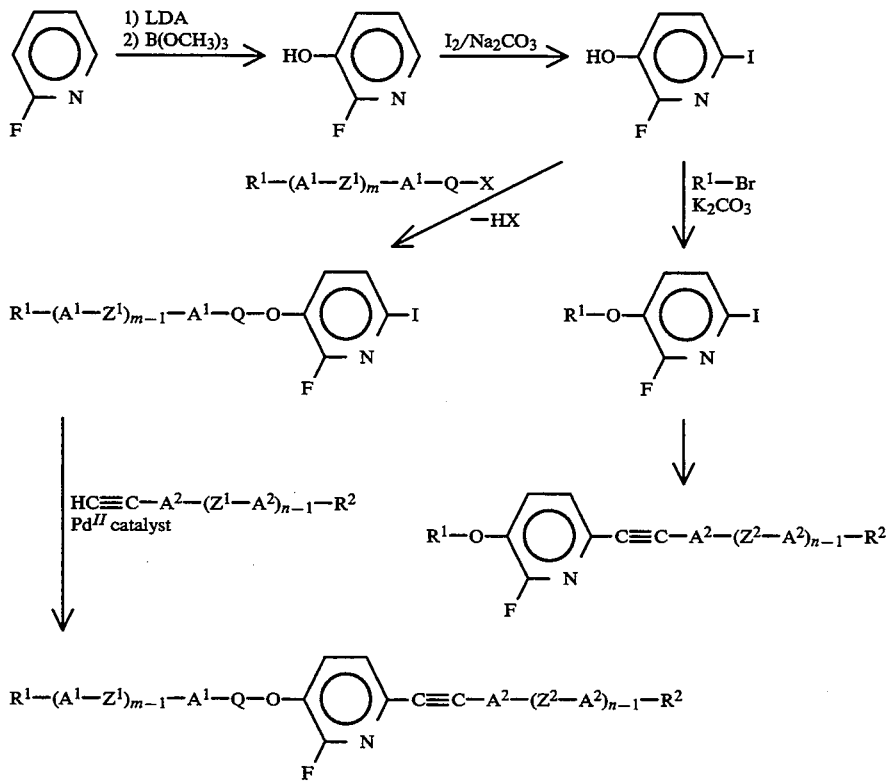

Scheme 7
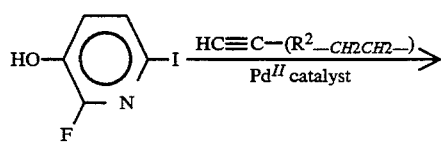 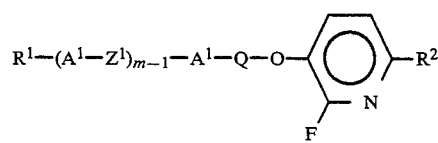
Scheme 8
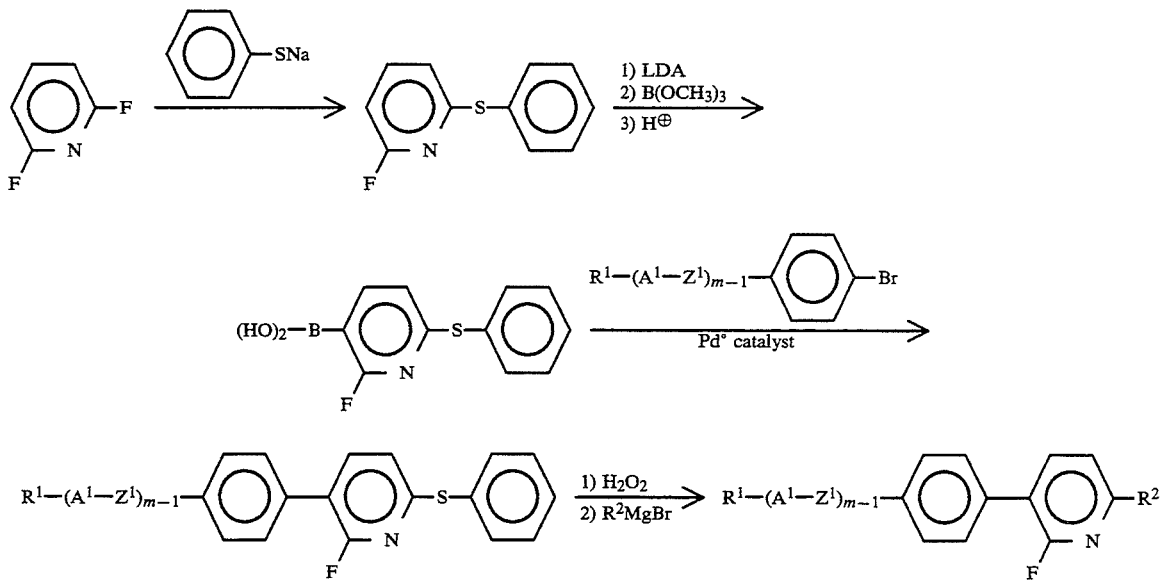
Scheme 9
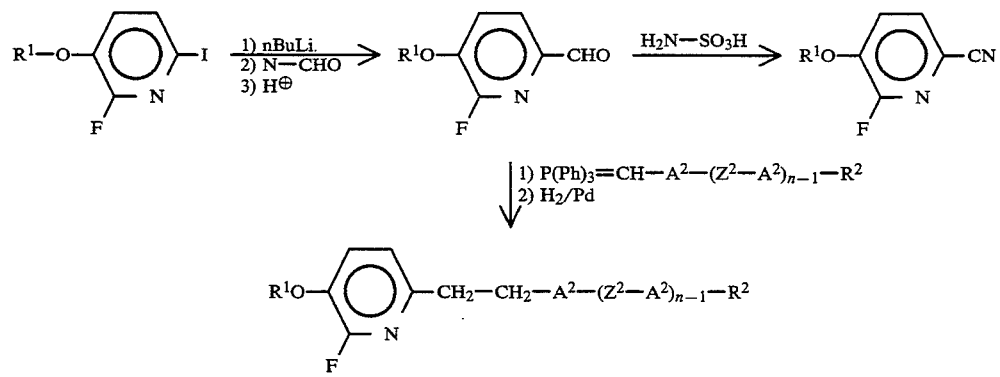
Scheme 10
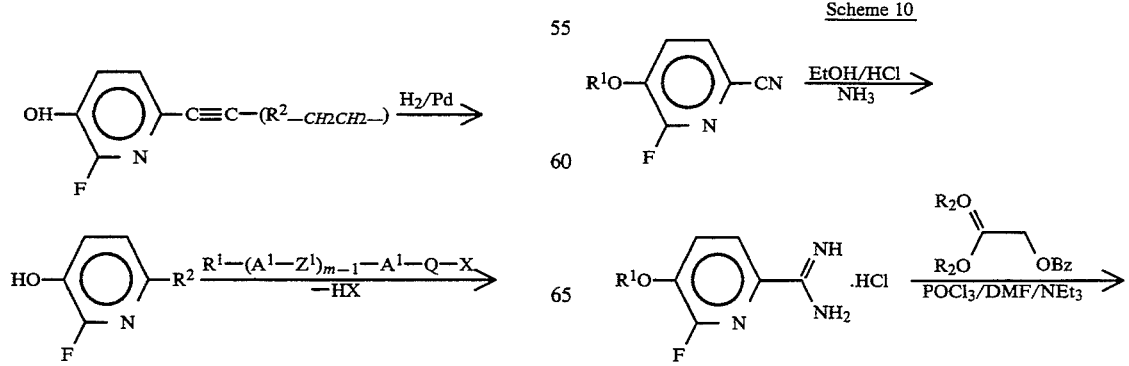

-continued
Scheme 10

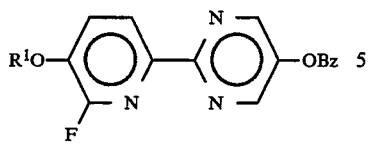

Bz = benzyl

The benzyl group can be removed hydrogenolytically, and the hydroxyl group can then be re-etherified or re-esterified by known methods.

The chiral compounds according to the invention can be prepared in accordance with the reaction schemes (I to VII) below.

Thus, compounds of the formula I in which the chiral radical R* has the formula IIIa where s=2 and p=1 can be prepared by preparing suitable precursors from optically active malic acid in accordance with the reaction scheme I:

Scheme I

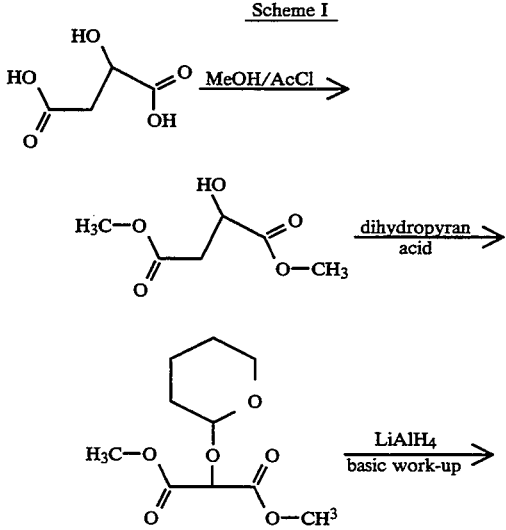

-continued
Scheme I

The synthesis has been described by Mori et al. as far as this stage (Ko Mori, T. Takigawa and T. Matsuo, Tetrahedron 35, 933–944 (1979)).

Meyers and Lawson later found that the chemical purity of the acetonide obtained by this route is only about 90% (A. I. Meyers and J. P. Lawson, THL 23 4883–4886 (1982)).

This notwithstanding, the free alcohol group of the acetonide can be etherified by one of the conventional methods (for example C. A. Brown and D. Barton, Synthesis (1974) 434 or B. R. Jursic, Tetrahedron 44, 6677–6680 (1988)).

The benzyl ether (K. Isaac and P. Kocienski, J. Chem. Soc., Chem. Commun. (1982) 460–462) is a particularly suitable protecting group since it can later easily be removed hydrogenolytically. After etherification, the isopropylidene ketal is hydrolyzed under standard conditions to give the 1,2-diol, and this is then converted into the corresponding epoxide under the reaction conditions of Di Fabio and Misiti (R. Di Fabio and D. Misiti, Gazetta Chimica Italiana 118, 209–210 (1988)).

Treatment of the acetonide with HBr/glacial acetic acid and subsequent reaction of the bromooxalkyl acetates obtained in this way with K pentoxide likewise gives the desired epoxides in accordance with Scheme II, according to the paper by U. Schmidt et al. (U. Schmidt, J. Tabiersky, F. Bartowiak and J. Wild, Angew. Chem. 92, 201–202 (1980)).

Scheme IIa

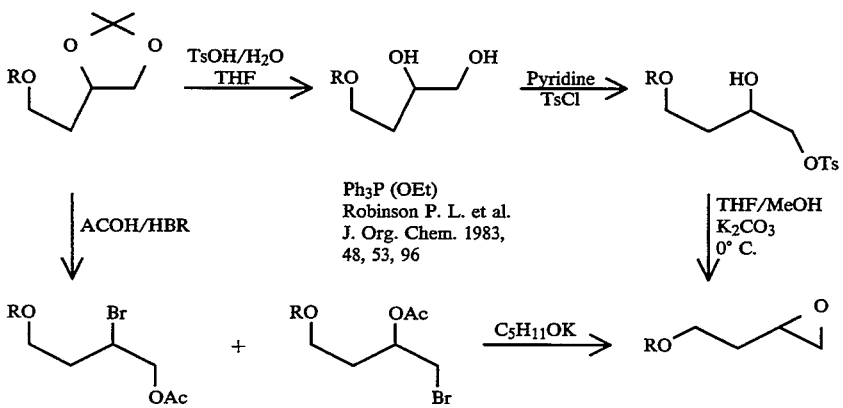

Reaction of the epoxide with organometallic compounds in accordance with Scheme IIa, preferably with Grignard compounds, with ring opening on the less-substituted carbon atom of the epoxide, gives, with high selectivity, the corresponding alcohol, which is fluorinated using DAST under standard conditions; hydrogenolysis gives the chiral alcohol, which is etherified using 5-hydroxypyridines.

Scheme IIb

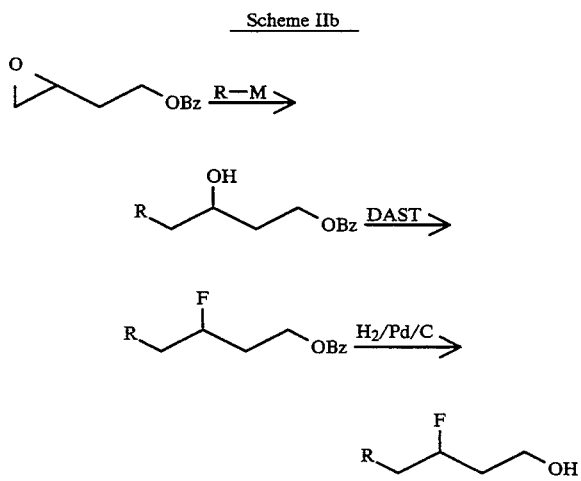

If the expoxide is opened using pyridine/HF (N. Mongelli, F. Animati et al., Synthesis 310 (1988)), the corresponding fluoroalcohol is obtained, which can subsequently be converted into the corresponding tosylate. Such tosylates are particularly suitable for alkylation of phenols and 5-hydroxypyridines in accordance with Scheme III or Scheme IV.

Scheme III

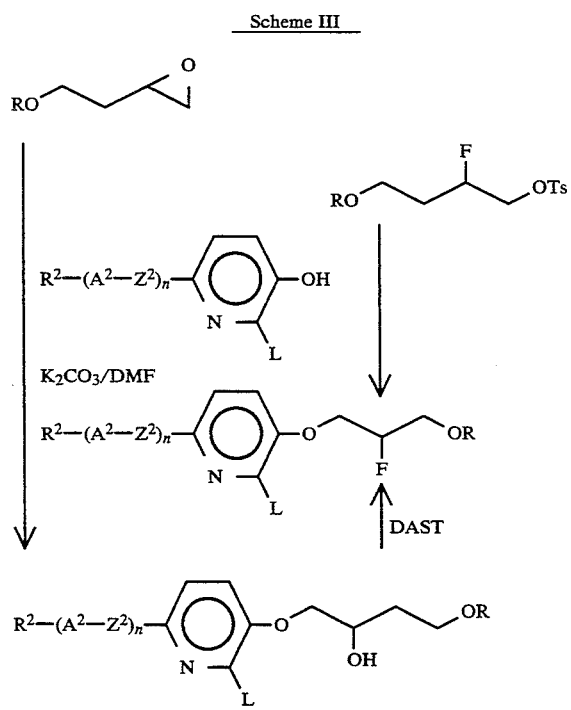

Scheme IV

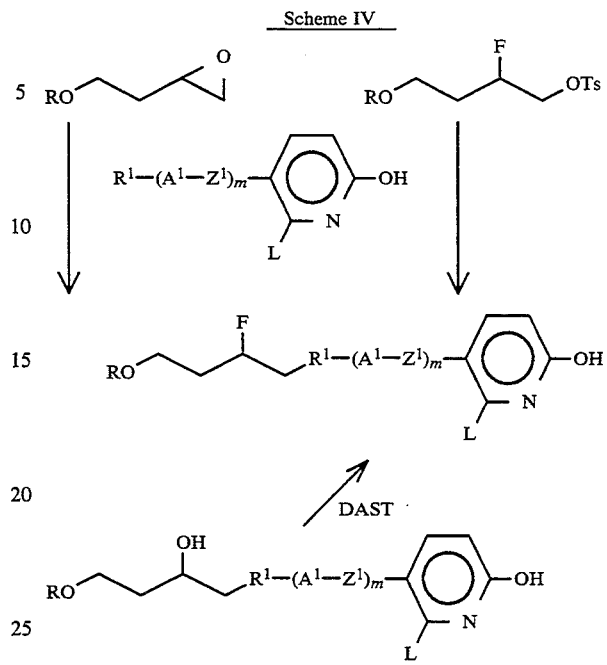

As the above reaction schemes show, the epoxide can also be reacted directly with phenols. The epoxide is opened in high selectivity at the less-substituted carbon atom to give the chiral secondary alcohol, which is then finally converted into the compounds according to the invention using DAST with inversion. Regarding the conventional reactions of alcohols with DAST, see: M. Hudlicky, Organic Reactions 35 513–637 (1987).

The compounds according to the invention where $Q^3 = $—O—CO— can be prepared from the corresponding benzyl ethers by hydrogenolysis and subsequent esterification. The synthesis scheme V below describes the preparation:

Scheme V

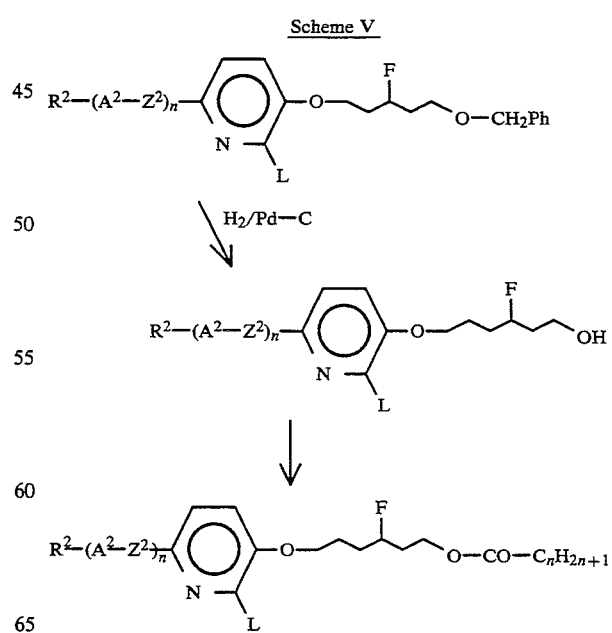

The compounds where $Q^3 = $—O—CO— are furthermore obtained by oxidation of the corresponding fluoroalcohols and subsequent esterification using mesogenic phenols in accordance with Scheme VI:

Scheme VI

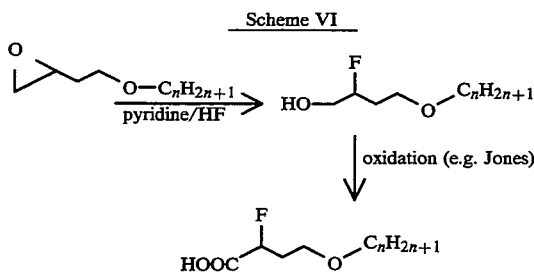

If racemization occurs during oxidation, the optically active fluoro acids can be isolated by separating the racemate by the method of Helmchen (Angew. Chem. 91, 65 (1979)).

CH-acidic compounds likewise open the epoxide in the presence of suitable bases to give the optically active secondary alcohol, which is then fluorinated using DAST with inversion. Preferred reaction routes are given in Scheme VII below.

Scheme VII

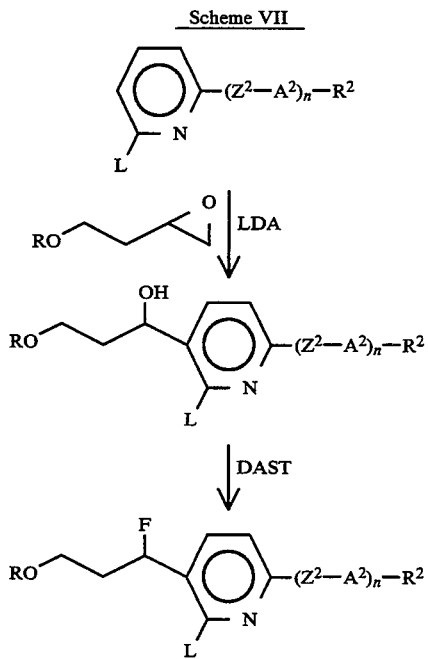

The compounds containing chiral radicals R* of the formula IIIa in which p is 1, s is 1 and $Q^3$ is O can be prepared analogously using the known epoxides of the formula

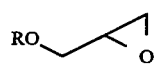

or the fluoroalcohols of the formula

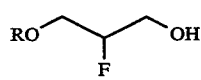

obtainable therefrom by conventional methods.

The compounds of the formula I are also suitable as components of nematic liquid-crystalline phases, in particular for ECB displays, but also for preventing reverse twist.

These liquid-crystalline phases according to the invention comprise 2 to 25, preferably 3 to 15 components, including at least one compound of the formula I. The other constituents are preferably selected from nematic or nematogenic substances, in particular known substances, from the classes comprising the azoxybenzenes, benzylidene anilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexylpyridazines and N-oxides thereof, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolans and substituted cinnamic acids.

The most important compounds which are suitable as components of liquid-crystalline phases of this type can be characterized by the formula I''

in which L and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

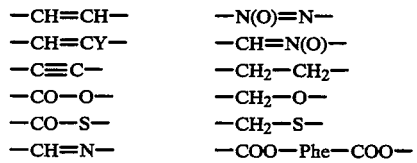

Y is halogen, preferably chlorine, or —CN, and

R' and R'' are alkyl, alkoxy, alkanoyloxy, alkoxycarbonyl or alkoxycarbonyloxy having up to 18, preferably up to 8, carbon atoms, or one of these radicals is alternatively CN, NC, $NO_2$, $CF_3$, F, Cl or Br.

In most of these compounds, R' and R'' are different from one another, one of these radicals usually being an alkyl or alkoxy group. However, other variants of the proposed substituents are also common. Many such substances or mixtures thereof are commercially available. All these substances can be prepared by methods which are known from the literature.

The phases according to the invention contain about 0.1 to 99%, preferably 10 to 95%, of one or more compounds of the formula I. Additionally preferred liquid-crystalline phases according to the invention are those which contain 0.1–40%, particularly 0.5–30%, of one or more compounds of the formula I. The phases according to the invention are prepared in a conventional manner. In general, the components are dissolved in one another, expediently at elevated temperature. By means of suitable additives, the liquid-crystalline phases according to the invention can be modified in a manner such that they can be used in all types of liquid-crystal display elements which have been disclosed hitherto.

Additives of this type are known to those skilled in the art and are described in detail in the literature. For example, conductive salts, preferably ethyldimethyldodecylammonium 4-hexyloxybenzoate, tetrabutylammonium tetraphenylborate or complex salts of crown ethers (cf., for example, I. Haller et al., Mol. Cryst. Liq. Cryst. Volume 24, pages 249–258 (1973)) can be added in order to improve the conductivity, pleochroic dyes can be added to produce colored guest-host systems or substances can be added to modify the dielectric anisotropy, the viscosity and/or the orientation of the nematic phases.

Substances of this type are described, for example, in DE-A 2,209,127, 2,240,864, 2,321,632, 2,338,281, 2,450,088, 2,637,430, 2,853,728 and 2,902,177.

The mixtures described are particularly suitable as components of liquid-crystal switching and display devices, in particular for the SSFLC cell described at the outset. This applies in particular to the so-called "virgin liquid-crystal structure", in which the smectic layers are at an angle to one another (chevron structures") and to the "bookshelf" or "quasi-bookshelf" geometry, in which the smectic layers are perpendicular or virtually perpendicular (see Y. Sato et al., Jap. J. Appl. Phys. Vol. 28, 483 (1989)).

In addition, the nematic mixtures containing compounds of the formula I, due to their broad nematic phase ranges and their high negative dielectric anisotropy, are particularly suitable as components of more highly twisted liquid-crystal displays, such as STN (for example GB 2,123,163) or OMI (for example M. Schadt, F. Leenhouts, Appl. Phys. Lett. 50, 236 (1987)), in which very high gradients of the characteristic line can be achieved (for example WO 89/08691).

In particular, the compounds of the formula IT are highly suitable as components of ECB displays (for example M. Schiekel, K. Fahrenschon, Appl. Phys. Lett. 19 391 (1971)), which [sic] they have very high values of the optical anisotropy ($\Delta n \geq 0.22$) and comparatively high-negative values of the dielectric anisotropy ($\Delta\epsilon \leq -5.0$).

The examples below are intended to illustrate the invention without representing a limitation. m.p.=melting point, c.p.=clearing point. Above and below, percentages are percent by weight; all temperatures are given in degrees Celsius. "Customary work-up" means that water is added, the mixture is extracted with methylene chloride, the organic phase is separated off, dried and evaporated, and the product is purified by crystallization and/or chromatography.

In addition:

| In addition: | |
|---|---|
| C | denotes crystalline |
| N | denotes nematic |
| S | denotes smectic |
| I | denotes isotropic. |

The numbers between these symbols indicate the respective phase-transition temperature in °C. The following abbreviations are also used:

| n-BuLi | n-butyllithium |
|---|---|
| DAST | diethylaminosulfur trifluoride |
| DCC | dicyclohexylcarbodiimide |

-continued

| DEAD | diethyl azodicarboxylate |
|---|---|
| DMF | dimethylformamide |
| LDA | Lithian [sic] diisopropylamide (prepared from equimolar amounts of n-BuLi and diisopropylamine) |
| THP | tetrahydrofuran |
| TP | triphenylphosphine |
| TPP | tetrakis (triphenylphosphine)palladium (0) |

EXAMPLE 1

1A 1-(trans-4-Pentylcyclohexyl)-4-(6-chloropyridin-2-yl)benzene

A mixture of 0.23 mol of 4-(trans-4-pentylcyclohexyl)phenylboric acid, 0.23 mol of 2,6-dichloropyridine, 5 mmol of TPP, 230 ml of a 2 molar sodium carbonate solution and 400 ml of toluene are heated at the boil for 1 hour. The reaction mixture is cooled, and 200 ml of hexane and 200 ml of water are added. The organic phase is separated off, the solvent is removed by evaporation, and the pure product is obtained by chromatography on silica gel using toluene/hexane 3:1 as the eluent.

1B

2-[4-(trans-4-Pentylcylcohexyl)phenyl]-5-hydroxy-2-chloropyridine [sic]

A mixture of 327.5 mmol of 1A and 10 ml of THF is added dropwise at $-65°$ C. to a mixture of 42 mmol of LDA and 40 ml of THF, and the mixture is stirred for 15 minutes. 38.1 mmol of trimethyl borate are subsequently added dropwise. The mixture is warmed to $-20°$ C., and 3.5 ml of glacial acetic acid and 5 ml of water are added. The mixture is warmed to room temperature, and 9 ml of $H_2O_2$ (30%) are added. The mixture is stirred for 20 hours and distributed between 200 ml of water and 200 ml of THF. The organic phase is separated off and shaken with a dilute ammonium iodide solution in order to remove peroxides.

After removal of the solvent by distillation, the product is processed further without purification.

IC 2-[4-(trans-4-Pentylcyclohexyl)phenyl]-5-ethoxy-2-chloropyridine

A mixture of 33.5 mmol of 1B, 34.2 mmol of TP, 34.2 mmol of DEAD, 34.2 mmol of ethanol and 200 m [sic] of THF is stirred for 20 hours at room temperature. Customary work-up and chromatography give the pure product, C 116.0 N 150.4 I, $\Delta\epsilon = -5.3$.

The following are prepared analogously

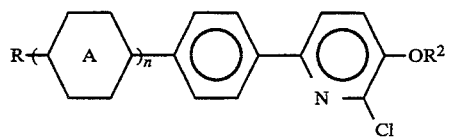

| $R^1$ | n | A | $R^2$ |
|---|---|---|---|
| $C_3H_7$ | 0 | — | $C_2H_5$ |
| $C_5H_{11}$ | 0 | — | $C_2H_5$ |
| $C_8H_{17}$ | 0 | — | $C_2H_5$ |
| $C_8H_{17}$ | 0 | — | $C_8H_{17}$ |

-continued $$R \left( A \right)_n - \bigcirc - \underset{N}{\bigcirc}\underset{Cl}{-OR^2}$$

| $R^1$ | n | A | $R^2$ |
|---|---|---|---|
| $C_3H_7$ | 1 | (cyclohexyl) | $C_8H_{17}$ |
| $C_5H_{11}$ | 1 | (cyclohexyl) | $C_8H_{17}$ |
| $C_8H_{17}$ | 1 | (cyclohexyl) | $C_8H_{17}$ |
| $C_3H_7$ | 1 | (phenyl) | $C_3H_7$ |
| $C_5H_{11}$ | 1 | (phenyl) | $C_3H_7$ |
| $C_8H_{17}$ | 1 | (phenyl) | $C_8H_{17}$ |

EXAMPLE 2

2A 2-Fluoro-6-phenylsulfonylpyridine

A mixture of 0.4 mol of 2,6-difluoropyridine, 0.6 mol of thiophenol, 0.6 mol of NaOH, 450 ml of water, 180 ml of toluene and 3.5 g of tetrabutylammonium bromide is refluxed for hours.

The mixture is cooled to room temperature, the organic phase is separated off, and the aqueous phase is extracted with hexane. The combined organic phases are washed with a saturated sodium chloride solution and dried using sodium sulfate. The solvent is evaporated, 22 g of a 35% $H_2O_2$ solution and 50 ml of glacial acetic acid are added to the residue, and the mixture is heated at the boil for 18 hours. Cooling, customary work-up and chromatography on silica gel using dichloromethane gives the pure product.

2B 2-(4-Octyloxyphenyl)-6-fluoropyridine

A mixture of 0.06 mol of 4-octyloxyphenylmagnesium bromide (prepared from 0.06 mol of 4-octyloxybromobenzene and 0.06 mol of 4-octyloxybromobenzene and 0.06 mol of magnesium) and 25 ml of THF is added at 30°–40° C. to a mixture of 0.05 mol of 2A and 15 ml of THF. The mixture is stirred at room temperature for 2 hours and subjected to customary work-up.

The unpurified product is processed further in accordance with 2C.

2C 2-(4-Octyloxyphenyl)-5-hydroxy-6-fluoropyridine

The product is obtained analogously to Example 1B [lacuna] 0.05 mol of 2B, 0.08 mol of LDA, 0.08 mol of trimethyl borate, and 0.16 mol of $H_2O_2$ (in the form of a 30% solution).

2D 2-(Octyloxyphenyl)-5-octyloxy-6-fluoropyridine

The product, C 81 $S_c$ 89 I, $\Delta\epsilon=-4.3$, $\Delta n=0.161$, is obtained analogously to Example 1C from 20 mmol of 2C, 20 mmol of octanol, 20 mmol of TP and 20 mmol of DEAD.

The following are prepared analogously:

$$R^1 \left( A \right)_n - B - \underset{N}{\bigcirc}\underset{F}{-R^2}$$

| $R^1$ | n | A | B | $R^2$ |
|---|---|---|---|---|
| $C_8H_{17}O$ | 0 | — | (phenyl) | $OC_{10}H_{21}$ C 86 $S_C$ 90.0 I |
| $C_8H_{17}$ | 0 | — | (phenyl) | $OC_8H_{17}$ C 38 $S_C$ 57 I, $\Delta\epsilon = -4.63$ |
| $C_{10}H_{21}O$ | 0 | — | (phenyl) | $OC_8H_{17}$ |
| $C_3H_7$ | 0 | — | (phenyl) | $OC_2H_5$ C 82 I, $\Delta\epsilon$ −7 |
| $C_5H_{11}$ | 0 | — | (phenyl) | $OC_2H_5$ C 64 I, $\Delta\epsilon$ −6.2 |
| $C_5H_{11}$ | 0 | — | (cyclohexyl) | $OC_4H_9$ |
| $C_3H_7$ | 0 | — | (phenyl) | $OC_4H_9$ C 59 I, $\Delta\epsilon$ −6 |
| $C_5H_{11}$ | 0 | — | (phenyl) | $OCH_3$ C 69 I, $\Delta\epsilon$ −6.2 |
| $C_5H_{11}$ | 1 | H (cyclohexyl) | (phenyl) | $OC_2H_5$ C 112 $S_A$ (105) N 189.7 I, $\Delta\epsilon = -5.3$ $\Delta n = 0.211$ |

-continued $$R^1 \!-\!\!\left(\!\!A\!\!\right)_{\!\!\overline{n}}\!\!-\!\!\left(\!\!B\!\!\right)\!\!-\!\!\left(\!\!\begin{array}{c}\\N\\F\end{array}\!\!\right)\!\!-\!R^2$$

| R¹ | n | A | B | R² |
|---|---|---|---|---|
| $C_8H_{17}$ | 1 | H | ⬡ | $OC_8H_{17}$ |
| $C_5H_{11}$ | 1 | H | ⬡ | $C_3H_7$ C 60 $S_G$ 86 $S_F$ 91 $S_A$ 124 N 150 I, $\Delta\epsilon = -3.05$ |
| $C_3H_7$ | 1 | H | H | $OC_2H_5$ C 81 $S_B$ 98 N 178.5 I $\Delta\epsilon = -6.13$ |
| $C_2H_5O$ | 0 | — | ⬡ | $C_3H_7$ |
| $C_2H_5O$ | 0 | — | ⬡ | $C_5H_{11}$ |
| $C_8H_{17}O$ | 0 | — | ⬡ | $C_{10}H_{21}$ |
| $C_{10}H_{21}O$ | 0 | — | ⬡ | $C_{10}H_{21}$ |
| $C_{10}H_{21}$ | 0 | — | ⬡ | $C_{10}H_{21}$ |

EXAMPLE 3

A solution of 0.1 mol of 2-(octylphenyl)-5-(2-hydroxy-5-oxaoctyloxy)-6-fluoropyridine (prepared by heating optically active 1,2-epoxy-5-oxaoctane, obtainable from malic acid, with 2C in the presence of dry potassium carbonate and methyl ethyl ketone as solvent) in methylene chloride is cooled to −40° C., and 0.11 mol of DAST is added dropwise thereto with exclusion of moisture. The reaction mixture is subsequently stirred for 12 hours with slow warming to room temperature. The reaction mixture is then hydrolyzed with ice cooling and washed with dilute sodium hydroxide solution and several times with water. The mixture is dried over magnesium sulfate, the solvent is removed on a rotary evaporator, and the crude product is purified by chromatography and by crystallization, giving optically active 2-(4-octyloxyphenyl)-5-(2-fluoro-5-oxaoctyloxy)-6-fluoropyridine.

The following compounds of the formula I1 are prepared analogously:

$$H_{2m+1}C_{\overline{m}}O\!\!-\!\!(CH_2)_{\overline{2}}\overset{*}{C}H\!\!-\!\!CH_2\!\!-\!\!O\!\!-\!\!\left(\!\!\begin{array}{c}\\N\\F\end{array}\!\!\right)\!\!-\!\!\left(\!\!\bigcirc\!\!\right)\!\!-\!OC_nH_{2n+1}$$
$$|\atop F$$

| m | n |
|---|---|
| 2 | 7 |
| 4 | 7 |
| 5 | 7 |
| 2 | 8 |
| 3 | 8 |
| 4 | 8 |
| 5 | 8 |
| 3 | 9 |
| 3 | 10 |

EXAMPLE 4

4-(6-Fluoro-5-octyloxypyridin-2-yl)-1-(2-fluoro-5-oxyoctyl)benzene [sic] is obtained analogously to Example 3 from 0.1 mol of 4-(6-fluoro-5-octyloxypyridin-2-yl)phenol (prepared as in Example 2 by hydrolysis of 4-(6-fluoro-5-octyloxypyridin-2-yl)-1-benzyloxybenzene) and 0.1 mol of optically active 1,2-epoxy-5-octane.

The following compounds of the formula I1 are prepared analogously:

$$R^1\!\!-\!\!\left(\!\!\begin{array}{c}\\N\\F\end{array}\!\!\right)\!\!-\!\!\left(\!\!\bigcirc\!\!\right)\!\!-\!O\!-\!CH_2\!-\!\overset{*}{C}H\!-\!(CH_2)_{\overline{2}}XC_nH_{2n+1}$$
$$|\atop F$$

| R¹ | n | X |
|---|---|---|
| $C_7H_{15}O$ | 3 | O |
| $C_9H_{19}O$ | 3 | O |
| $C_{11}H_{23}O$ | 3 | O |
| $C_8H_{17}$ | 3 | $CH_2$ |

EXAMPLE 4 a 4-(6-Fluoro-5-(2-fluoro-5-oxyoctyl)pyridin-2-yl)-1-octylbenzene [sic] 0.1 mol of 2 C (prepared as in Example 1) and 0.1 mol of optically active 2-fluoro-1-octanol are dissolved in 200 ml of THF, and 0.1 m [sic] of triphenylphosphine and 0.1 m [sic] of DEAD are added at RT. The mixture is stirred at RT for a further 2 hours and worked up by extraction: [lacuna]

$$R^1\!\!-\!\!\left(\!\!\bigcirc\!\!\right)\!\!-\!\!\left(\!\!\begin{array}{c}\\N\\F\end{array}\!\!\right)\!\!-\!OCH_2\!-\!\overset{*}{C}H\!-\!(CH_2)_n\!-\!CH_3$$
$$|\atop F$$

| R¹ | n | R¹ | n |
|---|---|---|---|
| $C_8H_{17}$ | 5 C 80 I | | |
| $C_7H_{15}O$ | 5 | $C_7H_{15}$ | 5 |

-continued

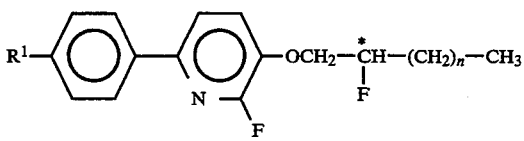

| R¹ | n | R¹ | n |
|---|---|---|---|
| C$_8$H$_{17}$O | 5 | C$_8$H$_{17}$ | 5 |
| C$_9$H$_{19}$O | 5 | C$_9$H$_{19}$ | 5 |
| C$_{10}$H$_{21}$O | 5 | C$_{10}$H$_{21}$ | 5 |

EXAMPLE 5

0.17 mol of DEAD dissolved in THF is added to a solution of 0.15 mol of 2C (prepared as in Example 1), 0.17 mol of L(—)-ethyl lactate and 0.15 mol of triphenylphosphine in 400 ml of THF. A reaction temperature of 50° C. should not be exceeded. The mixture is stirred at 50° C. for 1 hour and then at room temperature overnight. The solvent is then removed by distillation, the residue is dissolved in hot toluene, and the solution is then allowed to cool slowly. The precipitated triphenylphosphine oxide is removed by suction filtration, the filtrate is evaporated, the residue is purified by chromatography, giving ethyl 2-[2-(4-octyloxyphenyl)-6-fluoropyridin-5-yl]propionate.

EXAMPLE 6

Optically active benzyl lactate is etherified using 2C (prepared as in Example 1) by means of diethyl azodicarboxylate (DEAD)/triphenylphosphine, and the benzyl group is subsequently removed hydrogenolytically. The acid obtained in this way is converted as usual into the nitrile (oxalyl chloride, ammonia, thionyl chloride), giving optically active 2-(4-octyloxyphenyl)-5-(1-cyanoethoxy)-6-fluoropyridine.

EXAMPLE 7

A solution of 0.1 mol of DCC in methylene chloride is added at 0° C. to a mixture of 0.1 mol of 2C 0.1 mol of optically active 2-chloro-3-methylbutyric acid (prepared from valine) and a catalytic amount of 4-(N,N-dimethylamino)pyridine in 250 ml of methylene chloride. The mixture is subsequently stirred at room temperature for 12 hours, the precipitate is then filtered off with suction, and the filtrate is subjected to customary work-up, giving [2-(4-octyloxyphenyl)-6-fluoropyridine-5-yl ester] [sic].

EXAMPLE 8

0.2 mmol of bis(triphenylphosphine)palladium(II) chloride and 0.1 mmol of copper(I) iodide are added at room temperature to a mixture of 0.01 mol of 5-ethoxy-2-iodo-6-fluoropyridine (prepared from 2-fluoropyridine by reaction with lithium diisopropylamide, triethyl borate and hydrogen peroxide, iodination of the resultant 3-hydroxy-2-fluoropyridine, and subsequent etherification using iodoethane/potassium carbonate), 0.01 mol of 4-(trans-4-propylcyclohexyl)phenylacetylene (preparable, for example, by the method of Smith, Hoehn, Am. Soc. 63 (1941) 1175) and 40 ml of triethylamine, and the mixture is stirred for 12 hours. The reaction can be monitored by means of thin-layer chromatography. When the reaction is complete, the suspension is filtered, and the filtrate is evaporated. Purification by chromatography and/or crystallization gives 1-(5-ethoxy-6-fluoropyridin-2-yl)-1-[4-(trans-4-propylcyclohexyl)phenyl]acetylene.

The following are [sic] prepared analogously:
1-(5-Ethoxy-6-fluoropyridin-2-yl)-1-(4-pentylphenyl)acetylene, C 69 N (54.1) I Δε=—7.83, Δn =0.252.

EXAMPLE 9

A mixture of 0.1 mol of 2C, 0.1 mol of 1-bromoethoxyethane, 0.1 mol of sodium hydroxide, 20 ml of ethanol and 50 ml of water is heated at the boil for 2 hours. The mixture is cooled, dilute hydrochloric acid is added, and the aqueous phase is extracted with dichloromethane. The solvent is removed under reduced pressure, and the residue is purified by column chromatography, giving the product 2-(4-octyloxyphenyl)-5-(2-ethoxyethoxy)-6-fluoropyridine.

The following are prepared analogously:

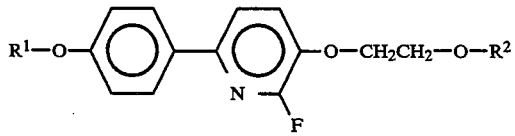

| R¹ | R² |
|---|---|
| C$_5$H$_{11}$ | C$_2$H$_5$ |
| C$_{11}$H$_{23}$ | C$_2$H$_5$ |
| C$_8$H$_{17}$ | C$_4$H$_9$ |
| C$_8$H$_{11}$ | CH$_3$ |
| C$_8$H$_{17}$ | C$_2$H$_4$—O—C$_2$H$_5$ |
| C$_5$H$_{11}$ | C$_2$H$_4$—O—C$_2$H$_5$ |
| C$_{11}$H$_{23}$ | C$_2$H$_4$—O—C$_2$H$_5$ |

The examples below relate to ferroelectric liquid-crystalline media.

EXAMPLE A

A liquid-crystalline medium is prepared which comprises:
5.8% of (2-hexyloxyphenyl)-5-heptylpyrimidine
5.8% of (2-octyloxyphenyl)-5-heptylpyrimidine
5.8% of (2-decyloxyphenyl)-5-heptylpyrimidine
1.1% of (2-p-octyloxyphenyl)-5-octylpyrimidine
1.1% of (2-p-nonyloxyphenyl)-5-octylpyrimidine
1.1% of (2-p-decyloxyphenyl)-5-octylpyrimidine
7.0% of 2-(4-octyloxyphenyl)-5-octyloxy-6-fluoropyridine
4.1% of 2-(4-heptyloxyphenyl)-5-dodecyloxy-6-fluoropyridine
4.1% of 2-(4-decyloxyphenyl)-5-undecyloxy-6-fluoropyridine
5.0% of 2-(4-octyloxy-2,3-difluorophenyl)-5-nonylpyrimidine
5.0% of 2-(4-heptyloxy-2,3-difluorophenyl)-5-nonylpyrimidine
5.0% of 2- ( 4-nonyloxy-2,3-difluorophenyl ) -5-nonylpyrimidine
18.0% of 2- ( 4-hexyloxyphenyl ) -5-hexyloxypyrimidine and
10% of optically active 2-[4-(2-fluorooctyloxy)-2,3-difluorophenyl]-5-heptylpyrimidine.

This medium has a broad S$_c$* phase range and high spontaneous polarization.

EXAMPLE B

A liquid-crystalline medium is prepared which comprises:

5.8% of 2 -(p-hexyloxyphenyl)-5-heptylpyrimidine
5.8% of 2 -(p-octyloxyphenyl)-5-heptylpyrimidine
5.8% of 2 -(p-decyloxyphenyl)-5-heptylpyrimidine
1.1% of 2 -(p-octyloxyphenyl)-5-octylpyrimidine
1.1% of 2-(p-nonyloxyphenyl)-5-octylpyrimidine
2.2% of 2-(p-decyloxyphenyl)-5-octylpyrimidine
5.0% of 2-(4-decyloxyphenyl)-5-dodecyloxy-6-fluoropyrimidine
10.1% of 2-(4-octyloxyphenyl-2-yl)-5-octyloxy-6-fluoropyrimidine
10.1% of 2-(5-decyloxypyridin-2-yl)-5-undecyloxypyrimidine
10% of 2-(4-octyloxy-2,3-difluorophenyl)-5-heptylpyrimidine
5% of 2-(4-octyloxy-2,3-difluorophenyl)-5-nonylpyrimidine
5% of 2-(4-heptyloxy-2,3-difluorophenyl)-5-nonylpyrimidine
5% of 2-(4-nonyloxy-2,3-difluorophenyl)-5-nonylpyrimidine
18% of 2-(p-hexyloxyphenyl)-5-hexyloxypyrimidine and
10% of optically active 2-[4-(2-fluorooctyloxy)phenyl]-5-octyloxypyridine This medium has an $S_c^*$ phase range of greater than 60° C. and high spontaneous polarization.

EXAMPLE C

To an achiral base mixture comprising
3.3% of 2-(4-hexyloxyphenyl)-5-heptylpyrimidine
3.3% of 2-(4-heptyloxyphenyl)-5-heptylpyrimidine
3.3% of 2-(4-octyloxyphenyl)-5-heptylpyrimidine
3.3% of 2-(4-nonyloxyphenyl)-5-heptylpyrimidine
7.7% of 2-(4-hexyloxyphenyl)-5-nonylpyrimidine
25.3% of 2-(4-nonyloxyphenyl)-5-nonylpyrimidine
30.8% of 4-(4'-octylbiphenyl-4-yl)-1-cyano-1-butylcyclohexane
15.4% of 4-(4'-heptylbiphenyl-4-yl)-1-cyano-1-hexylcyclohexane
6.6% of 1,4-bis[trans-4-pentylcyclohexyl]-1-cyanocyclohexane
which has the following phase transitions:

$S_c$ 76 $S_A$ 80 N 36 are added 10% of chiral 2-(4-octylphenyl)-5-(2-fluorooctyloxy)-6-fluoropyridine.
The ferroelectric medium exhibits:

$S_c^*$ 73 $S_A$ 78 CN 91 I

Spontaneous polarization (at 20° C.): 17.6 nC.cm$^{-1}$
Response time (at 20° C. and 15 V/μm): 85 μsec

EXAMPLE 10

10A 2-Propyn-1-yl-6-fluoropyridine

A mixture of 0.06 mol of propynylmagnesiumbromide and 25 ml of THF is added at 40°–40° C. [sic] to a mixture of 0.05 mol of 2A and 15 ml of THF. The mixture is stirred at room temperature for 2 hours and subjected to customary work-up. The unpurified product is processed further as in 10B.

10B 2-Propynyl-6-fluoropyridin-5-ylboric acid 0.05 mol of 10A, 0.08 mol of LDA and 0.08 mol of trimethyl borate are reacted with one another analogously to Example 1B. Aqueous work-up gives the unpurified product, which is processed further as in 10C.

10C 2-Propyl-6-fluoro-5-[4-(trans-4-pentylcyclohexyl)-phenyl]pyridine 0.02 mol of 10B is coupled with 0.02 mol of 4-(trans-4-pentylcyclohexyl)bromobenzene as in EP 0 354 434 in the presence of sodium bicarbonate and tetrakis[triphenylphosphine]palladium. Conventional work-up and purification by chromatography gives the alkyne intermediate as a colorless solid, which is hydrogenated using Pd charcoal in THF to give the alkyl compound, C 66 N 123 I.

The following are prepared analogously:

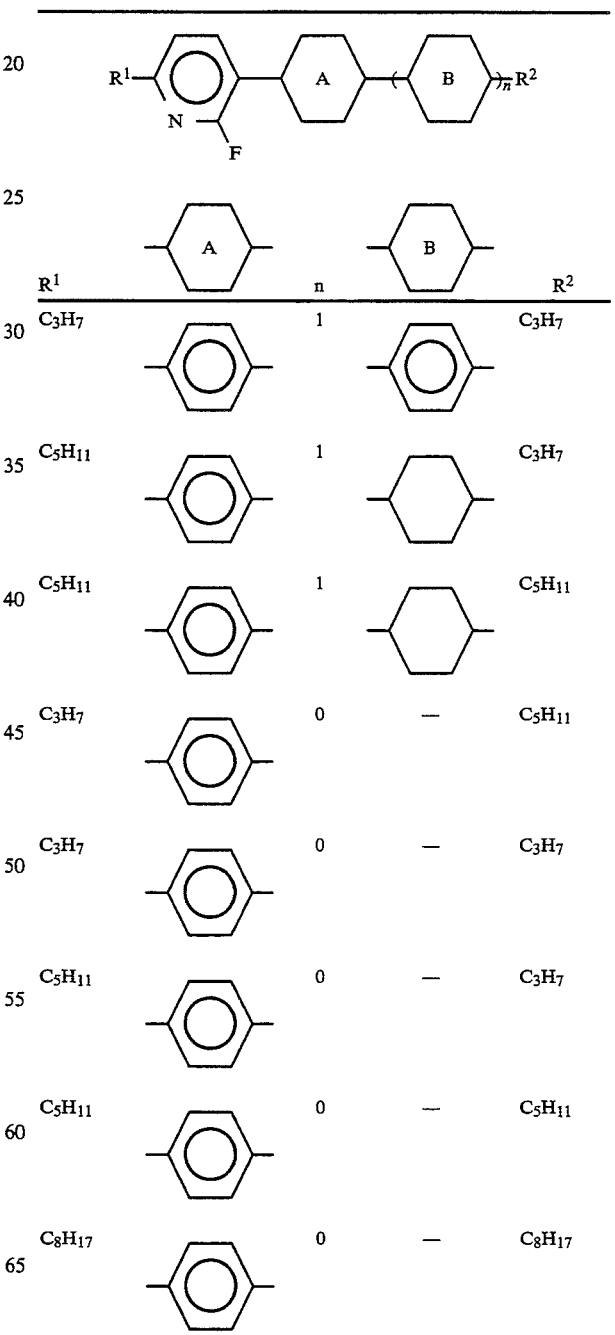

-continued

| R$^1$ | A | n | B | R$^2$ |
|---|---|---|---|---|
| C$_8$H$_{17}$ | | 0 | phenyl | C$_{10}$H$_{21}$ |
| C$_8$H$_{17}$ | | 0 | phenyl | OC$_8$H$_{17}$ |
| C$_{10}$H$_{21}$ | | 0 | phenyl | OC$_{10}$H$_{21}$ |
| C$_3$H$_7$ | cyclohexyl | 1 | cyclohexyl | C$_5$H$_{11}$ |
| C$_3$H$_7$ | cyclohexyl | 1 | cyclohexyl | C$_3$H$_7$ |
| C$_5$H$_{11}$ | cyclohexyl | 1 | cyclohexyl | C$_3$H$_7$ |
| C$_5$H$_{11}$ | cyclohexyl | 1 | cyclohexyl | C$_5$H$_{11}$ |

EXAMPLE D

A liquid-crystalline medium is prepared which comprises:
20.00% of 2-(p-heptyloxyphenyl)-5-nonylpyrimidine
20.00% of 2-(p-octyloxyphenyl)-5-nonylpyrimidine
20.00% of 2-(p-nonyloxyphenyl)-5-nonylpyrimidine
20.00% of 2-(p-hexyloxyphenyl)-5-hexyloxypyrimidine
6.00 % of 2-(p-octyloxyphenyl )-6-fluoro-5-octyloxypyrimidine
6.00 % of 2-(p-octyloxyphenyl )-6-fluoro-5-decyloxypyrimidine
6.66 % of 2-(p-octyloxyphenyl )-6-fluoro-5-octyloxypyrimidine This medium has the following phase transistions at C 5 S$_c$ 69 Ch 74 I.

EXAMPLE E

A ferroelectric, liquid-crystalline medium is prepared which comprises:
19.00% of 2-(p-heptyloxyphenyl)-5-nonylpyrimidine
19.00% of 2-(p-octyloxyphenyl)-5-nonylpyrimidine
19.00% of 2-(p-nonyloxyphenyl)-5-nonylpyrimidine
19.00% of 2-(p-hexyloxyphenyl)-5-hexyloxypyrimidine
6.34% of 2-(4-heptyloxy-2,3-difluorophenyl)-5-nonylpyrimidine
6.34% of 2-(4-octyloxy-2,3-difluorophenyl)-5-nonylpyrimidine
6.33% of 2-(4-nonyloxy-2,3-difluorophenyl)-5-nonylpyrimidine
5.00% of 2-(p-octylphenyl)-6-fluoro-5-(2-fluorooctyloxy)pyridine This medium has the following physical properties:
C 5 S$_c$* 63 S$_A$ 67 Ch 71 I
P$_s$ (20° C.): 6.8 nC.cm$^{-2}$
$\tau$ (20° C./15 V$\mu$m$^{-1}$): 84 $\mu$s

EXAMPLE F

A nematic liquid-crystalline ECB medium is prepared which comprises:
9.0% of p-(trans-4-propylcyclohexyl)-methoxybenzene
9.0% of p-(trans-4-propylcyclohexyl)-ethoxybenzene
9.0% of p-(trans-4-propylcyclohexyl)-butoxybenzene
5.0% of 4-ethyl-4'-methoxytolan
5.0% of 4-methyl-4'-ethoxytolan
4.0% of 2,2',3,3'-tetrafluoro-4-butoxy-4'-propyltolan
4.0% of 2,2',3,3'-tetrafluoro-4-butoxy-4'-pentyltolan
13.0% of 2,3-difluoro-4-ethoxy-4'-propyltolan
13.0% of 2,3-difluoro-4-ethoxy-4'-pentyltolan
5.0% of 4-(trans-4-propylcyclohexyl)-4'-methoxytolan
5.0% of 4-(trans-4-propylcyclohexyl)-4'-ethoxytolan
5.0% of 4-(trans-4-propylcyclohexyl)-4'-propoxytolan
2.0% of 2,3-difluoro-4-ethoxyphenyltrans,trans-4-propylcyclohexylcyclohexane-4'-carboxylate 7.0% of 2-(trans,trans-4-propylcyclohexylcyclohexan-4'-yl)-6-fluoro-5-ethoxypyridine 5.0% of 1-(p-pentylphenyl)-2-(6-fluoro-5-ethoxypyridin-2-yl)ethyne

EXAMPLE G

A nematic liquid-crystalline ECB medium is prepared which comprises:
9.0% of p-(trans-4-propylcyclohexyl)-methoxybenzene
9.0% of p-(trans-4-propylcyclohexyl)-ethoxybenzene
9.0% of p-(trans-4-propylcyclohexyl) -butoxybenzene
5.0% of 4-ethyl-4'-methoxytolan
5.0% of 4-methyl-4'-ethoxytolan
4.0% of 2,2',3,3'-tetrafluoro-4-butoxy-4'-propyltolan
4.0% of 2,2',3,3'-tetrafluoro-4-butoxy-4'-pentyltolan
13.0% of 2,3-difluoro-4-ethoxy-4'-propyltolan
13.0% of 2,3-difluoro-4-ethoxy-4 '-pentyltolan
5.0% of 4-(trans-4-propylcyclohexyl)-4'-methoxytolan
5.0% of 4-(trans-4-propylcyclohexyl)-4'-ethoxytolan
5.0% of 4-(trans-4-propylcyclohexyl)-4'-propoxytolan
6.0% of 4-(trans,trans-4-propylcyclohexylcyclohexan-4'-yl )-2,3-difluoroethoxybenzene
5.0% of 4'-(trans-4-pentylcyclohexyl)-2,3-difluoro-4-ethoxybiphenyl
3.0% of 2-(p-pentylphenyl)-6-fluoro-5-ethoxypyridine

EXAMPLE H

A nematic liquid-crystalline ECB medium is prepared which comprises:
9.0% of p-(trans-4-propylcyclohexyl)-methoxybenzene
9.0% of p-(trans-4-propylcyclohexyl)-ethoxybenzene
9.0% of p-(trans-4-propylcyclohexyl)-butoxybenzene
5.0% of 4-ethyl-4'-methoxytolan
5.0% of 4-methyl-4'-ethoxytolan
4.0% of 2,2',3,3'-tetrafluoro-4-butoxy-4'-propyltolan
4.0% of 2,2',3,3'-tetrafluoro-4-butoxy-4'-pentyltolan 13.0% of 2,3-difluoro-4-ethoxy-4'-propyltolan
13.0% of 2,3-difluoro-4-ethoxy-4'-pentyltolan
5.0% of 4-(trans-4-propylcyclohexyl)-4'-methoxytolan
5.0% of 4-(trans-4-propylcyclohexyl)-4'-ethoxytolan
5.0% of 4-(trans-4-propylcyclohexyl)-4'-propoxytolan
3.0% of 2,3-difluoro-4-ethoxyphenyl trans,trans-4-propylcyclohexylcyclohexan-4'-ylcarboxylate
5.0% of 4-(trans,trans-4-propylcyclohexylcyclohexan-4'-yl)-2,3-difluoroethoxybenzene
4.0% of 2-(p-pentylphenyl)-6-fluoro-5-ethoxypyridine The physical properties of the media for ECB displays of Examples F, G and H are shown in Table I below:

TABLE I

| Example | F | G | H |
| --- | --- | --- | --- |
| Clearing point (°C.) | +83 | +84 | +83 |
| Viscosity (mm²s⁻¹) at 20° C. | 25 | <25 | <25 |
| Δn | +0.218 | +0.217 | +0.214 |
| V$_{(90,0,20)}$ (V) | 2.4 | 2.8 | 2.8 |
| V$_{(10,0,20)}$ (V) | 2.6 | 2.9 | 2.9 |

We claim:
1. 3,6-Disubstituted 2-halopyridines of the formula I

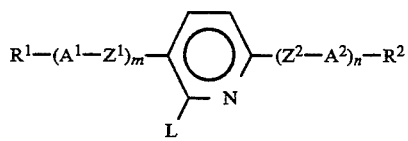

where
and R$^{1'}$ are each, independently of one another, an alkyl or alkenyl radical having up to 15 carbon atoms which is unsubstituted or monosubstituted by CN, halogen or CF$_3$, it also being possible for one or more CH$_2$ groups in these radicals to be replaced, in each case independently of one another, by —S—, —O—, —CO—, —CO—O—, —O—CO— or —O—CO—O— in such a manner that S and/or O atoms are not linked directly to one another, and one of the radicals R$^1$ and R$^2$ is alternatively halogen, —CF$_3$, —OCF$_3$ or OCHF$_2$,
A$^1$ and A$^2$ are each, independently of one another, a
(a) trans-1,4-cyclohexylene radical in which, in addition, one or more non-adjacent CH$_2$ groups may be replaced by —O— and/or —S—,
(b) 1,4-phenylene radical in which, in addition, one or two CH groups may be replaced by N,
(c) radical from the group comprising 1,3-cyclobutylene, 1,3-bicyclo[1.1.1]pentylene, 1,4-cylohexenylene, 1,4-bicyclo[2.2.2]octylene, piperidine-1,4-diyl, naphthalene-2,6 -diyl, decahydronaphthalene-2,6-diyl and 1,2,3,4-tetrahydronaphthalene-2,6-diyl, it being possible for the radicals (a) and (b) to be substituted by CN or halogen,
Z$^1$ and Z$^2$ are each, independently of one another, —CH$_2$—CH$_2$—, —C≡C—, —CH$_2$O—, —OCH$_2$—, —CO—O—, —O—CO—, —CH=N—, —CH$_2$S—, —SCH$_2$—, a single bond or an alkylene group having 3 to 6 carbon atoms in which, in addition, one CH$_2$ group may be replaced by —O—, —CO—O—, —O—CO—, —CH-halogen- or —CHCN—,
L is F, m is 0, 1 or 2,
n is 0, 1 or 2, and
m+n is 1, 2 or 3,
with the proviso that
Z$^2$ is —CH$_2$CH$_2$—, —C≡C—, —CH$_2$O—, —CO—O— or a single bond.

2. Halopyridines according to claim 1, in which n is 1 or 2, and at least one of the radicals A$^1$ and A$^2$ is optionally fluorine-substituted 1,4-phenylene, 1,4-cyclohexylene, pyrimidine-2,5-diyl or pyridine-2,5-diyl.

3. Liquid-crystalline medium having at least two components, characterized in that at least one component is a compound of the formula I of claim 1.

4. Electrooptical display, comprising as a dielectric material, a liquid-crystalline medium according to claim 6.

5. Ferroelectric crystalline medium having at least one chiral component and at least one achiral component, characterized in that at least one component contains a liquid-crystalline compound which contains a group of the formula

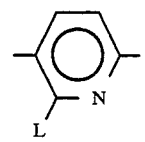

in which L is F, as a structural element, characterized in that it contains at least one compound of the formula I according to claim 1.

6. Ferroelectric crystalline medium having at least one chiral component and at least one achiral component, characterized in that at least one component contains a liquid-crystalline compound which contains a group of the formula

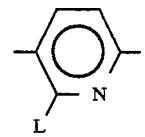

in which L is F, as a structural element, characterized in that it contains, as dielectric, a liquid-crystalline medium according to claim 3.

7. A ferroelectric liquid crystalline medium as in claim 3, wherein L is F.

8. A ferroelectric liquid crystalline medium as in claim 3, additionally comprising a phenyl pyrimidine of the formula

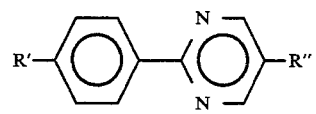

wherein R' and R" are each C$_{2\text{-}10}$-straight-chain alkyl or alkoxy groups.

9. A ferroelectric liquid crystalline medium as in claim 7, comprising a compound of formula I

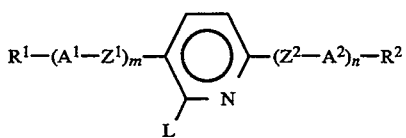

wherein
- $A^1$ and $A^2$ are each, independently of one another, a
  - (a) trans-1,4-cyclohexylene radical in which, in addition, one or more non-adjacent $CH_2$ groups may be replaced by —O— and/or —S—,
  - (b) 1,4-phenylene radical in which, in addition, one or two CH groups may be replaced by N,
  - (c) radical from the group comprising 1,3-cyclobutylene, 1,3-bicyclo[1.1.1]pentylene, 1,4-cyclohexenylene, 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl it being possible for the radicals (a) and (b) to be substituted by CN or halogen,
- $Z^1$ and $Z^2$ are each, independently of one another, —$CH_2$—$CH_2$—, —$CH_2O$—, —$OCH_2$—, —CO—O—, —O—CO—, —CH=N—, —$CH_2S$—, —$SCH_2$—, a single bond or an alkylene group having 3 to 6 carbon atoms in which, in addition, one $CH_2$ group may be replaced by —O—, —CO—O—, —O—CO—, —CH-halogen- or —CHCN—,
- L is F,
- m is 0, 1 or 2,
- n is 0, 1 or 2, and
- m+n is 1, 2 or 3, with the proviso that where $R^2$ is halogen, CN, —$CF_3$, $OCF_3$, $OCHF_2$ or alkoxy, n is 1 or 2, and $Z^2$ is —$CH_2$—$CH_2$—, —C≡C—, —$CH_2O$—, —CO—O— or a single bond, wherein one of the radicals $R^1$ and $R^2$ is a chiral group selected from the group consisting of compounds of formulae III, IIIa, and IIIc,
wherein formula III is as follows:

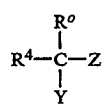  III wherein
- $R^4$ is a group of the formula $(CH_2)_n$—$Q^3$—$C_oH_{2no+1}$, in which $Q^3$ is —O—, —O—CO—, or a single bond; n is 0, 1 or 2; and o is 1 to 7;
- Y is CN, halogen, or $CH_3$;
- Z is a single bond or —$(CH_2)_p$—, in which one $CH_2$ group may be replaced by —O—, —O—CO—, or —CO—O—, and p is 1, 2, 3, 4, 5, or 6; and
- $R^o$ is H or $CH_3$, with the proviso that only one of the groups $R^o$, $R^4$, and Y is $CH_3$;
wherein formula IIIa is as follows:

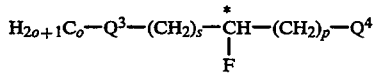  IIIa wherein
o is 1 to 7; $Q^3$ and $Q^4$ are each independently —O—, —CO—O—, or a single bond; s is 1 or 2; and p is 0 or 1; and
wherein formula IIIc is as follows:

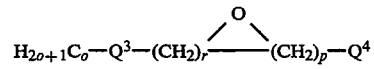  IIIc in which $Q^3$ and $Q^4$ are each independently —O—, —CO—O—, or a single bond; r is 1 or 2; and p is 0 or 1.

10. 3,6-Disubstituted 2-halopyridines of the formula I′

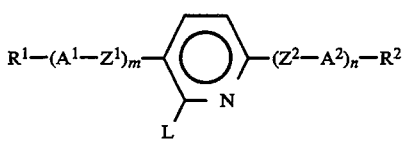  I′ wherein
- $R^1$ and $R^2$ are each, independently of one another, an alkyl or alkenyl radical having up to 15 carbon atoms which is unsubstituted or monosubstituted by CN, halogen or $CF_3$, it also being possible for one or more $CH_2$ groups in these radicals to be replaced, in each case independently of one another, by —S—, —O—, —CO—, —CO—O—, —O—CO— or —O—CO—O— in such a manner that S and/or O atoms are not linked directly to one another,
- $A^1$ and $A^2$ are each, independently of one another, a
  - (a) trans-1,4-cyclohexylene radical in which, in addition, one or more non-adjacent $CH_2$ groups may be replaced by —O— and/or —S—,
  - (b) 1,4-phenylene radical in which, in addition, one or two CH groups may be replaced by N, it being possible for the radicals (a) and (b) to be substituted by CN or halogen,
- $Z^1$ and $Z^2$ are each, independently of one another, —$CH_2$—$CH_2$—, —C≡C—, —$CH_2O$—, —$OCH_2$—, —CO—O—, —O—CO—, —CH=N—, —$CH_2S$—, —$SCH_2$—, a single bond or an alkylene group having 3 to 6 carbon atoms in which, in addition, one $CH_2$ group may be replaced by —O—, —CO—O—, —O—CO—, —CH-halogen- or —CHCN—,
- L is F
- m is 0, 1 or 2,
- n is 1 or 2, and
- m+n is 1, 2 or 3.

11. A liquid crystalline medium having at least two components, wherein at least one component is a compound of formula I′ of claim 10.

12. A matrix liquid crystal display which contains, as a dielectric, a liquid crystal medium according to claim 11.

13. A liquid crystal switching and display device containing a ferroelectric liquid crystalline medium, outer plates, electrodes, at least one alignment layer and, optionally, additional assistant layers which contain at least one liquid crystal compound of formula I′ of claim 10.

* * * * *

UNITED STATES PATENT AND TRADEMARK OFFICE
CERTIFICATE OF CORRECTION

PATENT NO. : 5,389,291                                    Page 1 of 2
DATED       : February 14, 1995
INVENTOR(S) : Volker Reiffenpath, et al It is certified that error appears in the above-indentified patent and that said Letters Patent is hereby corrected as shown below:

Claim 1; column 45, line 34: Before "and" insert -- $R^1$ --.

Claim 1; column 45, line 34: After "and" change "$R^1$" to -- $R^2$ --.

Claim 1; column 45, line 61: Change "--C--C--," to -- --C≡C-- --.

Claim 1; column 45, line 61: Change "--$CH_{2a}$--," to -- --$CH_2O$--, --.

Claim 1, column 45, line 61: change " OCH--" to -- --$OCH_2$--, --.

Claim 1, column 45, line 62, Delete "CH--" and insert -- -$CH_2S$--.
             line 63, Delete "$_2S$--".

UNITED STATES PATENT AND TRADEMARK OFFICE
CERTIFICATE OF CORRECTION

PATENT NO. : 5,389,291
DATED : February 14, 1995
INVENTOR(S) : Voler Reiffenrath et al It is certified that error appears in the above-indentified patent and that said Letters Patent is hereby corrected as shown below:

Claim 1, column 46, line 4: After "that" insert -- where $R^2$ is halogen, CN, $-CF_3$, $OCF_2$, $OCHF_2$ or alkoxy, n is 1 or 2, --.

Claim 1; column 46, line 5: Change "$-C-C-$" to -- $-C\equiv C-$, --.

Claim 4, column 46, line 18: Change "6" to -- 3 --.

Claim 9, column 47, lines 42 & 61: After "formula" change "IIia" to -- IIIa --.

Claim 9, column 48, line 2: Delete "I" and insert -- 1 --.

Signed and Sealed this

Twenty-first Day of November, 1995

Attest:

BRUCE LEHMAN

*Attesting Officer*   Commissioner of Patents and Trademarks